US011170148B2

(12) United States Patent
Tsunoda et al.

(10) Patent No.: US 11,170,148 B2
(45) Date of Patent: Nov. 9, 2021

(54) SIMULATION APPARATUS, SIMULATION METHOD, AND STORAGE MEDIUM

(71) Applicant: NIPPON CONTROL SYSTEM CORPORATION, Tokyo (JP)

(72) Inventors: Dai Tsunoda, Kanagawa (JP); Nobuyasu Takahashi, Kanagawa (JP)

(73) Assignee: NIPPON CONTROL SYSTEM CORPORATION, Tokyo (JP)

( * ) Notice: Subject to any disclaimer, the term of this patent is extended or adjusted under 35 U.S.C. 154(b) by 48 days.

(21) Appl. No.: 16/622,048

(22) PCT Filed: Mar. 27, 2018

(86) PCT No.: PCT/JP2018/012398
§ 371 (c)(1),
(2) Date: Dec. 12, 2019

(87) PCT Pub. No.: WO2018/230090
PCT Pub. Date: Dec. 20, 2018

(65) Prior Publication Data
US 2021/0150114 A1 May 20, 2021

(30) Foreign Application Priority Data

Jun. 13, 2017 (JP) .............................. JP2017-115799

(51) Int. Cl.
*G06F 30/398* (2020.01)
*G06F 30/25* (2020.01)
(Continued)

(52) U.S. Cl.
CPC ............ *G06F 30/398* (2020.01); *G06F 30/25* (2020.01); *A61N 5/00* (2013.01); *G01N 23/00* (2013.01);
(Continued)

(58) Field of Classification Search
CPC ...... G06F 30/398; G06F 30/25; G06F 30/392; G03F 1/00; A61N 5/00; G01N 23/00; G21K 5/00; G21K 5/10; H01J 37/08
(Continued)

(56) References Cited

U.S. PATENT DOCUMENTS 7,685,556 B2  3/2010 Fukuhara et al.
2008/0201684 A1  8/2008 Krasnoperova
(Continued)

FOREIGN PATENT DOCUMENTS

DE    10214247 A1  10/2003
JP   2008-65246 A   3/2008
(Continued)

OTHER PUBLICATIONS

International Search Report issued in corresponding International Application No. PCT/JP2018/012398, dated Jun. 12, 2018, with English translation.
(Continued)

*Primary Examiner* — Phallaka Kik
(74) *Attorney, Agent, or Firm* — McDermott Will & Emery LLP

(57) ABSTRACT

A simulation apparatus includes: a factor amount converting information storage unit in which factor amount converting information, which is information indicating correspondence between low-fidelity information and high-fidelity information, is stored; a writing pattern information storage unit in which writing pattern information is stored; an ADI simulation unit that performs an ADI simulation using one or more evaluation points, for a writing pattern indicated by the writing pattern information, thereby acquiring one or more factor amounts; a converting unit that acquires high-fidelity information, which is one or more factor amounts, corresponding to the low-fidelity information, which is one
(Continued)

or more factor amounts, using the factor amount converting information; and an etching simulation unit that performs an etching simulation using the one or more factor amounts acquired by the converting unit.

8 Claims, 15 Drawing Sheets

(51) Int. Cl.
*G06F 30/392* (2020.01)
*G03F 1/00* (2012.01)
*A61N 5/00* (2006.01)
*G01N 23/00* (2006.01)
*G21K 5/10* (2006.01)
*H01J 37/08* (2006.01)

(52) U.S. Cl.
CPC .............. *G03F 1/00* (2013.01); *G06F 30/392* (2020.01); *G21K 5/10* (2013.01); *H01J 37/08* (2013.01)

(58) Field of Classification Search
USPC ......... 716/106, 55, 54, 51; 430/4, 5; 378/34, 378/35; 700/98, 121; 250/491.21, 250/492.21
See application file for complete search history.

(56) References Cited

U.S. PATENT DOCUMENTS

| | | | |
|---|---|---|---|
| 2009/0210838 A1* | 8/2009 | Al-Imam | G03F 1/36 716/106 |
| 2009/0233193 A1 | 9/2009 | Tanaka et al. | |
| 2009/0307649 A1 | 12/2009 | Pramanik et al. | |
| 2014/0089870 A1 | 3/2014 | Mos et al. | |
| 2015/0067619 A1* | 3/2015 | Hsuan | G03F 7/70441 716/53 |
| 2017/0068762 A1 | 3/2017 | Shimizu | |

FOREIGN PATENT DOCUMENTS

| | | |
|---|---|---|
| JP | 2009-210635 A | 9/2009 |
| JP | 2010-519572 A | 6/2010 |
| JP | 2011-44656 A | 3/2011 |
| JP | 2011-133795 A | 7/2011 |
| JP | 2017-49938 A | 3/2017 |
| WO | 2012049901 A1 | 4/2012 |

OTHER PUBLICATIONS

Extended European Search Report dated Mar. 2, 2021, issued in EP Application No. 18816640.9.

* cited by examiner

| α | β |
|---|---|
| 0 | 0 |
| 0.110973 | 0.09414 |
| 0.218646 | 0.183325 |
| 0.277352 | 0.23125 |
| 0.321821 | 0.269372 |
| 0.358642 | 0.303043 |
| 0.389582 | 0.334861 |
| 0.415296 | 0.3638 |
| 0.436238 | 0.389729 |
| 0.465955 | 0.431764 |
| 0.483197 | 0.460694 |
| 0.492279 | 0.478745 |
| 0.4990284 | 0.4964532 |
| 0.5 | 0.5 |
| 0.5009716 | 0.5035468 |
| 0.507721 | 0.521255 |
| 0.516803 | 0.539306 |
| 0.534045 | 0.568236 |
| 0.563762 | 0.610271 |
| 0.584704 | 0.6362 |
| 0.610418 | 0.665139 |
| 0.641358 | 0.696957 |
| 0.678179 | 0.730628 |
| 0.722648 | 0.76875 |
| 0.781354 | 0.816675 |
| 0.889027 | 0.9058802 |
| 1 | 1 |

FIG.3

| knot | coefficient |
|---|---|
| 0 | 0.0001038443 |
| 0 | 0.0315668451 |
| 0.110973 | 0.0935587171 |
| 0.218646 | 0.1696519083 |
| 0.277352 | 0.2265518610 |
| 0.321821 | 0.2657607625 |
| 0.358642 | 0.2997256727 |
| 0.389582 | 0.3314906557 |
| 0.415296 | 0.3616661958 |
| 0.436238 | 0.3956460273 |
| 0.465955 | 0.4307914470 |
| 0.483197 | 0.4636954205 |
| 0.492279 | 0.4840556777 |
| 0.4990284 | 0.4945602891 |
| 0.5 | 0.5000000000 |
| 0.5009716 | 0.5054397109 |
| 0.507721 | 0.5159443223 |
| 0.516803 | 0.5363045795 |
| 0.534045 | 0.5692085530 |
| 0.563762 | 0.6043539727 |
| 0.584704 | 0.6383338042 |
| 0.610418 | 0.6685093443 |
| 0.641358 | 0.7002743273 |
| 0.678179 | 0.7342392375 |
| 0.722648 | 0.7734481390 |
| 0.781354 | 0.8303480917 |
| 0.889027 | 0.9064412829 |
| 1 | 0.9684331549 |
| 1 | 0.9998961557 |

FIG.4

| ID | Factor amount converting information | | | |
|---|---|---|---|---|
| | Factor identifier | Shape identifier | Low-fidelity information | High-fidelity information |
| 1 | Opening angle $\Omega$ | Rectangular shape (three sides) | 0 | 0 |
| | | | 0.110973 | 0.09414 |
| | | | 0.218646 | 0.183325 |
| | | | ⋮ | ⋮ |
| | | | 1 | 1 |
| 2 | Opening angle $\Omega$ | Recessed shape | ⋮ | ⋮ |
| | | | 0.313763 | 0.28542 |
| | | | ⋮ | ⋮ |
| ⋮ | ⋮ | ⋮ | ⋮ | ⋮ |
| 3 | Area ratio u | Projecting shape | ⋮ | ⋮ |
| | | | 0.27683 | 0.23864 |
| | | | ⋮ | ⋮ |
| 4 | Area ratio u | Stepped shape | ⋮ | ⋮ |
| | | | 0.113763 | 0.09542 |
| | | | ⋮ | ⋮ |
| ⋮ | ⋮ | ⋮ | ⋮ | ⋮ |

FIG.11

SIMULATION APPARATUS, SIMULATION METHOD, AND STORAGE MEDIUM

CROSS-REFERENCE OF RELATED APPLICATIONS

This application is the U.S. National Phase under 35 U.S.C. § 371 of International Patent Application No. PCT/JP2018/012398, filed on Mar. 27, 2018, the entire disclosure of which the Application is incorporated by reference herein.

TECHNICAL FIELD

The present invention relates to a simulation apparatus and the like for performing a mask process simulation.

BACKGROUND ART

Conventionally, there are shape simulation apparatuses including: a flux calculating unit that calculates flux of particles that are incident on a surface of a wafer on which a mask has been placed; and a shape calculating unit that performs time-series development on coordinates of multiple calculation points set on the surface of the wafer based on the calculated incident flux, and calculates a surface shape of the wafer (see Patent Document 1, for example).

CITATION LIST

Patent Document
Patent Document 1: JP 2011-44656A

SUMMARY OF INVENTION

Technical Problem

However, in the above-described shape simulation apparatus, it is necessary to set a large number of calculation points in order to precisely perform calculation, and thus the speed of the simulation is low.

Furthermore, also in other conventional simulation apparatuses, the level of precision and the speed of a simulation are in a trade-off relationship, and thus it is difficult to perform a mask process simulation accurately at high speed.

Solution to Problem

A first aspect of the present invention is directed to a simulation apparatus including: a factor amount converting information storage unit in which factor amount converting information, which is information indicating correspondence between low-fidelity information and high-fidelity information, is stored, wherein the low-fidelity information is one or more factor amounts with a low level of precision acquired using a first number of evaluation points, and the high-fidelity information is one or more factor amounts with a high level of precision acquired using a second number of evaluation points, the second number being larger than the first number; a writing pattern information storage unit in which writing pattern information related to a writing pattern is stored; an ADI simulation unit that performs an ADI simulation using one or more evaluation points, for the writing pattern indicated by the writing pattern information, thereby acquiring one or more factor amounts; a converting unit that acquires high-fidelity information, which is one or more factor amounts, corresponding to the low-fidelity information, which is one or more factor amounts, using the factor amount converting information; and an etching simulation unit that performs an etching simulation using the one or more factor amounts acquired by the converting unit.

With this configuration, it is possible to perform a mask process simulation accurately at high speed.

Furthermore, a second aspect of the present invention is directed to the simulation apparatus according to the first aspect, further including: a judging unit that acquires residuals respectively at the one or more evaluation points using a result of the etching simulation obtained by the etching simulation unit, and judges whether or not an error is small enough to satisfy a predetermined condition, using the one or more residuals; and a pattern information changing unit that, in a case in which the judging unit judges that the predetermined condition is not satisfied, changes the writing pattern information using the residuals of the one or more evaluation points; wherein the processes by the ADI simulation unit, the converting unit, and the etching simulation unit are repeated until the judging unit judges that the predetermined condition is satisfied.

With this configuration, it is possible to perform a mask process simulation more accurately at high speed.

In the second aspect of the present invention, it is also possible that, for example, the ADI simulation unit arranges one or more evaluation points on the outer periphery of a writing pattern, and, until an accumulated energy for each of the one or more evaluation points becomes close to a predetermined threshold enough to be regarded as being equal to the threshold, repeats processing for calculating the accumulated energy, and moving each evaluation point to the outer side of the outer periphery in a case in which the accumulated energy is greater than the threshold or moving the evaluation point to the inner side of the outer periphery in a case in which the accumulated energy is less than the threshold, and the judging unit acquires residuals respectively at the one or more evaluation points after the accumulated energy becomes close to the predetermined threshold enough to be regarded as being equal to the threshold, and judges whether or not an error is small using the acquired one or more residuals.

With this configuration, it is possible to perform a mask process simulation more accurately at high speed.

Furthermore, a third aspect of the present invention is directed to the simulation apparatus according to the first or second aspect, wherein, in the factor amount converting information storage unit, two or more pieces of factor amount converting information are stored in association with a shape identifier for identifying a shape of a writing pattern, the simulation apparatus further includes a shape identifier acquiring unit that acquires a shape identifier for identifying a shape of a writing pattern that is specified with the writing pattern information, and the converting unit acquires high-fidelity information, which is one or more factor amounts, corresponding to the low-fidelity information, which is one or more factor amounts, using factor amount converting information corresponding to the shape identifier acquired by the shape identifier acquiring unit.

With this configuration, it is possible to perform a proper mask process simulation according to writing patterns with multiple shapes.

Furthermore, a fourth aspect of the present invention is directed to the simulation apparatus according to any one of the first to third aspects, wherein the factor amount converting information is a pair of pieces of information consisting of the low-fidelity information that is a numerical value and the high-fidelity information that is a numerical value.

With this configuration, it is possible to perform a mask process simulation accurately at high speed.

Furthermore, a fifth aspect of the present invention is directed to the simulation apparatus according to any one of the first to third aspects, wherein the factor amount converting information is a function in which the low-fidelity information is taken as input and the high-fidelity information is taken as output.

With this configuration, it is possible to perform a mask process simulation accurately at high speed.

Furthermore, a sixth aspect of the present invention is directed to the simulation apparatus according to the fifth aspect, wherein the function is a polynomial function or a spline function.

With this configuration, it is possible to perform a mask process simulation accurately at high speed.

Advantageous Effects of Invention

According to the present invention, it is possible to perform a mask process simulation accurately at high speed.

BRIEF DESCRIPTION OF DRAWINGS

FIG. 3 is a table showing an example of factor amount converting information constituted by a set of pairs of numerical values in the embodiment.

FIG. 4 is a table showing an example of a set of pairs each consisting of a knot and a coefficient in a spline function in the embodiment.

FIG. 11 is a data structure table of factor amount converting information in the embodiment.

DESCRIPTION OF EMBODIMENT

Figure 1:
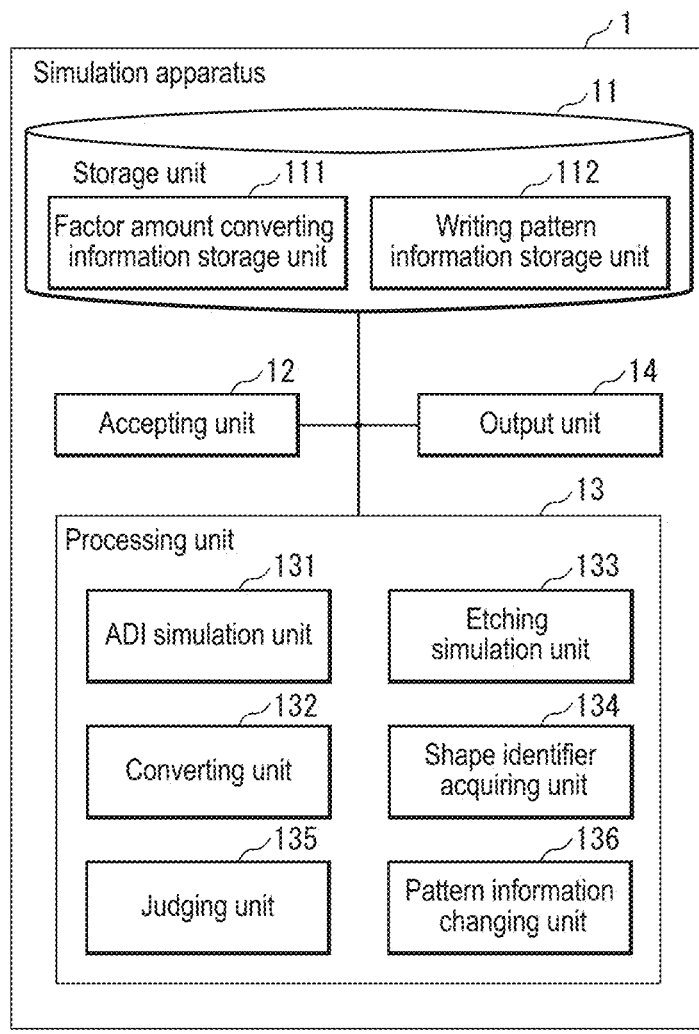
FIG. 1 is a block diagram of a simulation apparatus in an embodiment.

Hereinafter, an embodiment of a simulation apparatus and the like will be described with reference to the drawings. It should be noted that constituent elements denoted by the same reference numerals in the embodiments perform similar operations, and thus a description thereof may not be repeated.

In this embodiment, a simulation apparatus for performing a mask process simulation will be described.

A mask process simulation (hereinafter, it may be simply referred to as a "simulation") is a collective term for various simulations related to a photomask production process. The various simulations are a later-described ADI (after development inspection) simulation, a later-described etching simulation, or the like.

The photomask production process is, for example, a series of steps for producing a photomask that is used for semiconductor elements, printed wiring boards, or the like. The series of steps may be, for example, the following steps 1 to 5.

(Step 1) A step of applying resist to a mask blank. A mask blank is a material for photomasks, and is obtained by forming a light-blocking thin film on a substrate made of a glass or semiconductor wafer or the like. Resist is a composition in which, when irradiated with electron beams, light, or the like, physical properties such as a molecular weight or a solubility of the portion irradiated with the electron beams, light, or the like change.

(Step 2) A step of writing a figure such as a circuit using electron beams or the like on a mask blank to which resist has been applied. It is also possible that two or more pieces of writing pattern information are prepared in advance, and a figure is written by combining one or at least two pieces of writing pattern information.

(Step 3) A step of developing the resist on which the figure has been written. The developing is, for example, placing resist in a developer, thereby dissolving the portion irradiated with electron beams or the like, while leaving the portion not irradiated with electron beams or the like as a protective film against etching.

(Step 4) A step of etching the mask blank after development using ions, gas, or the like. Only the portions of the mask blank from which resist has been removed are etched by ions or the like, and the portions protected by resist are not etched.

(Step 5) A step of removing the resist from the mask blank after etching.

In the above-described series of steps, the line width of a contour line (hereinafter, it may be referred to as a "resist contour") of the writing pattern formed in the resist through the development in Step 3 is typically different from a line width defined by the writing pattern information. The reason for this seems to be that, for example, electrons of beams continue to move even after colliding against resist molecules and impart energy also to portions other than those irradiated with the beams. That is to say, electron beams emitted to an irradiation target region having resist scatter about the irradiation target region, and thus a region whose physical properties change does not exactly match the irradiation target region, and a line width change occurs.

An ADI simulation may also be said to be a simulation for acquiring information related to such a resist contour. The information related to a resist contour may be, for example, information indicating a resist contour, or may be information indicating a line width change in a resist contour.

The ADI simulation may be performed, for example, in a model-based manner using one or more evaluation points arranged along a contour line of a writing pattern indicated by one piece of writing pattern information. The evaluation points are points that are arranged on a writing pattern, and are points that are to be evaluated in various simulations such as ADI. The model that is used in an ADI simulation may be, for example, a threshold model. Although described later in detail, in a threshold model-based ADI simulation, the one or more evaluation points are repeatedly subjected to processing for searching for a position at which an energy value E of energy accumulated by electron beams at each evaluation point matches a threshold Eth, while moving the evaluation point, and a set of one or more searched positions that are positions that were searched for was acquired.

The information indicating a resist contour may be, for example, a set of one or more searched positions that were searched for in this manner, or may be a numerical formula or the like indicating a line extending along the one or more searched positions. The line extending along the searched positions may be, for example, a set of straight lines linking the searched positions, or may be a curved line such as a Bézier Curve acquired from the one or more searched positions. The line width change in a resist contour may be represented as, for example, a set of one or more vectors extending from the initial positions of the one or more evaluation points arranged on the contour line of the writing model to the searched positions that were searched for in this manner.

In addition, the line width of a contour line formed in the substrate through the etching in Step 4 is typically different from a line width defined by the writing pattern information. The reason for this seems to be that a line width change corresponding to the line width change that has occurred in the resist after development occurs also in the mask blank after etching, and, furthermore, a line width change occurs in the mask blank after etching due to, for example, shadowing or a loading effect.

The shadowing may also be said to be a phenomenon in which, for example, when the depth of a contour line is relatively greater with respect to the width thereof, the amount of ions that are obliquely incident decreases, and thus the speed at which a mask blank is etched is lowed, and the line width relatively decreases. The loading effect may also be said to be a phenomenon in which, for example, the amount of ions that are supplied to a point having densely arranged contour lines is insufficient compared with that to a point having sparsely arranged contour lines, and thus the speed at which a mask blank is etched is lowed, and the line width relatively decreases. Both phenomena are known, and a detailed description thereof has been omitted.

The etching simulation may also be said to be a simulation for acquiring information related to a contour line formed in a mask blank through etching as described above. In this embodiment, in particular, a line width change in a contour line formed in a mask blank through etching is acquired.

The etching simulation is performed, for example, in a model-based manner using one or more factor amounts acquired for each of the one or more evaluation points in the above-described ADI simulation. The model may be, for example, a variable bias model. Although described later in detail, in a variable bias model-based etching simulation, one or more factor amounts are acquired for each of the one or more evaluation points. A factor amount may also be said to be information representing a local shape at the evaluation points of the writing pattern. The factor amount is, for example, a numerical value of a factor such as an opening angle $\theta$ or an area ratio u, but there is no limitation to this, as long as it is information capable of representing a local shape of a writing pattern.

The opening angle $\Omega$ may also be said to be, for example, a numerical value indicating a ratio of a depth relative to a width of a contour line described above in regards to the shadowing. The area ratio u may also be said to be, for example, a numerical value indicating sparseness and density of contour lines described above in regards to the loading effect. The opening angle Q and the area ratio u will be described later in detail.

The line width change in a contour line formed in a mask blank through etching (hereinafter, it may be referred to as an "etch contour") may be regarded, for example, as a function of the one or more factor amounts. The function indicating a line width change $\delta$ in an etch contour at each of the one or more evaluation points may be specifically represented, for example, as $\delta=f(\Omega, u)$ using the opening angle $\Omega$ and the area ratio u acquired for the evaluation points.

Incidentally, in a resist contour according to the ADI simulation, not only does the line width change but an edge portion is rounded. Accordingly, in order to precisely perform an ADI simulation, it is necessary to arrange a large number of evaluation points such that a rounded shape of an edge portion can be represented. However, in conventional techniques, the processing speed of the ADI simulation is lowered in accordance with an increase in the number of evaluation points.

Furthermore, in the etching simulation, it is necessary to acquire an opening angle $\Omega$ and an area ratio u at each of the one or more searched points acquired in the ADI simulation, and the processing speed thereof is lowered in accordance with an increase in the number of evaluation points.

Thus, the simulation apparatus of this embodiment makes it possible to perform a mask process simulation accurately at high speed, by using factor amount converting information.

The factor amount converting information is information for converting one or more factor amounts. The conversion of one or more factor amounts is conversion from one or more factor amounts with a low level of precision to one or more factor amounts with a high level of precision. The one or more factor amounts with a low level of precision are one or more factor amounts acquired using a first number of evaluation points, and, in the description below, such one or more factor amounts may be referred to as low-fidelity information. The first number is one or at least two. For example, it is preferable that one or more evaluation points are arranged for each of the two or more sides constituting one writing pattern. Note that, in order to acquire low-fidelity information, typically, it is sufficient that one evaluation point is arranged for each side.

The one or more factor amounts with a high level of precision are one or more factor amounts acquired using a second number of evaluation points, the second number being larger than the first number, and, in the description below, such one or more factor amounts may be referred to as high-fidelity information. The second number is two or more. For example, when one evaluation point is arranged for each side in order to acquire low-fidelity information, it is preferable that, in order to acquire high-fidelity information, for example, several to several tens of, more specifically approximately 10 to 20 evaluation points are arranged for each side.

The simulation apparatus of this embodiment acquires low-fidelity information by arranging, in advance, the first number of evaluation points for one writing pattern, and also acquires high-fidelity information by arranging the second number of evaluation points for the writing pattern. It is preferable that two or more pairs of low-fidelity information and high-fidelity information are acquired, for example, for each of the two or more types of writing patterns.

The factor amount converting information is information indicating correspondence between low-fidelity information and high-fidelity information acquired for one writing pattern in this manner. It is preferable that, for example, the simulation apparatus acquires and accumulates factor amount converting information for each of the two or more types of writing patterns in advance. The representing format, the data structure, and the like of the factor amount converting information will be described later.

For example, the simulation apparatus acquires writing pattern information corresponding to a figure that is to be formed through etching, and arranges the first number of evaluation points on a writing pattern indicated by the writing pattern information and performs an ADI simulation, thereby acquiring one or more factor amounts that are low-fidelity information. Next, using factor amount converting information corresponding to the writing pattern information, the simulation apparatus acquires high-fidelity information that is high-fidelity information corresponding to the low-fidelity information, and that is one or more factor amounts acquired using the second number of evaluation points, the second number being larger than the first number, and performs an etching simulation using the one or more factor amounts that are the acquired high-fidelity information. Accordingly, it is possible to perform a simulation accurately at high speed.

Furthermore, in this embodiment, a simulation apparatus will be described that can correct errors using this sort of simulation result. The errors and their correction will be described later.

FIG. 1 is a block diagram of a simulation apparatus 1 in this embodiment. The simulation apparatus 1 includes a storage unit 11, an accepting unit 12, a processing unit 13, and an output unit 14. The storage unit 11 includes a factor amount converting information storage unit 111 and a writing pattern information storage unit 112. The processing unit 13 includes an ADI simulation unit 131, a converting unit 132, an etching simulation unit 133, a shape identifier acquiring unit 134, a judging unit 135, and a pattern information changing unit 136.

In the storage unit 11, various types of information may be stored. The various types of information are, for example, the above-described factor amount converting information, later-described writing pattern information, or the like.

In the factor amount converting information storage unit 111, one or at least two pieces of factor amount converting information are stored. As described above, the factor amount converting information is information indicating correspondence between low-fidelity information, which is one or more factor amounts with a low level of precision acquired for one writing pattern using the first number of evaluation points, and high-fidelity information, which is one or more factor amounts with a high level of precision acquired for the writing pattern using the second number of evaluation points, the second number being larger than the first number.

For example, if two or more pieces of writing pattern information related to various shapes such as a rectangle or a projection are stored in the later-described writing pattern information storage unit 112, factor amount converting information is stored for each of the two or more pieces of writing pattern information, in the factor amount converting information storage unit 111. The factor amount converting information for each piece of writing pattern information is, for example, factor amount converting information related to a rectangular writing pattern, factor amount converting information related to a recessed writing pattern, or the like.

As described above, the factor amount is information representing a local shape of a writing pattern, and is, for example, a value of a factor such as an opening angle Ω or an area ratio u.

The opening angle Ω is an angle of an opening of resist at one evaluation point. The opening of resist is the portion of a mask blank after development, at which the resist has been removed therefrom and the surface of the mask blank is exposed. The opening of resist may also be said to be, for example, a groove with a width corresponding to the line width of the resist contour and a depth corresponding to the thickness of the resist described above.

Alternatively, the opening of resist may also be said to be, for example, a set of one or at least two polygons formed by linking, with straight lines, one evaluation point that is one of three or at least four evaluation points constituting a resist contour, and that is located at the height of the surface of the mask blank, and each of the other two or at least three evaluation points that are located higher than the surface of the mask blank by the thickness of the resist.

The opening angle Ω is acquired by dividing an opening of resist into one or at least two triangles corresponding to the one or at least two polygons, and executing, for example, integration calculation as Numerical Formula 1 on each triangle obtained through division.

$$\Omega = \int_{\phi 1}^{\phi 2} \int_{0}^{atan\left(\frac{h}{r(\phi)}\right)} f(\theta) d\theta d\phi \quad \text{Numerical Formula 1}$$

In Numerical Formula 1, is an azimuth, as viewed from one vertex corresponding to the one evaluation point among three vertices constituting the triangle, of each of the other two vertices. Namely, φ1 is an azimuth of a first vertex of the other two vertices, and φ2 is an azimuth of a second vertex.

Figure 2:
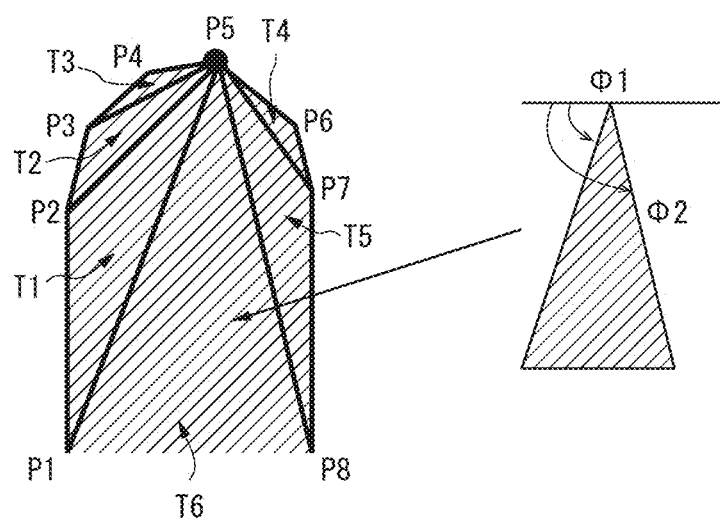
FIG. 2 is a diagram showing an example of triangulation in the embodiment.

FIG. 2 shows an example of triangulation. The triangulation of this example shows a case in which an opening defined by eight evaluation points P1 to P8 is divided into six triangles T1 to T6. For example, focusing on a triangle T6 defined by three vertices P1, P5, and P8, an azimuth 1, as viewed from the vertex P5 corresponding to the one evaluation point, of the first vertex P1 of the other two vertices is an angle formed by a straight line extending from the vertex P5 to the vertex P1 with respect to a predetermined reference line. In a similar manner, an azimuth 2 of the second vertex P8 as viewed from the vertex P5 is an angle formed by a straight line extending from the vertex P5 to the vertex P8 with respect to the reference line.

Furthermore, in Numerical Formula 1, θ is an elevation angle, as viewed from one vertex corresponding to the one evaluation point among three vertices constituting the triangle, of each of the other two vertices. For example, focusing on the triangle T6 in FIG. 2, the azimuth changes in a range of φ1 to φ2, whereas the elevation angle θ changes in a range of 0 to a tan(h/r(φ)). In this example, h is the thickness of the resist, and r(φ) is a horizontal distance to a point at which a straight line corresponding to the azimuth intersects the resist contour.

Accordingly, the opening angle Ω can be acquired, for example, by integrating a predetermined function f(θ) using the elevation angle θ as a parameter in the elevation angle direction in a range of 0 to atan(h/r(φ)), and further integrating it in the azimuth direction in a range of φ1 to φ2, as shown in Numerical Formula 1.

The area ratio u is a density of resist contours at one evaluation point. The area ratio u may be represented, for example, as the amount of contour lines that are located within a rang having a predetermined area centered about the one evaluation point (e.g., the number of grooves, the length of grooves, a value obtained by multiplying them, etc.). The area ratio can be acquired, for example, by dividing an opening into triangles or quadrangles, and performing convolution using the Gaussian function.

If one or more factor amounts are acquired for each of the two or more types of factors such as the opening angle Ω and the area ratio u described above for one writing pattern, it is preferable that factor amount converting information is stored for each of the two or more types of factors in the factor amount converting information storage unit 111. The one or more factor amounts for each factor may be, for example, numerical values "0.11", "0.21", . . . of the opening angle Q, which is a type of factor, or numerical values "0.09", "0.18", . . . of the area ratio u, which is another type of factor. The factor amount converting information for each factor is, for example, factor amount converting information related to the opening angle Ω, factor amount converting information related to the area ratio u, or the like.

It is more preferable that, in the factor amount converting information storage unit 111, the factor amount converting information is stored for each combination of two or more pieces of writing pattern information and two or more types of factors. The factor amount converting information for each combination of writing pattern information and a factor is, for example, factor amount converting information related to an opening angle Ω of a rectangular writing pattern, factor amount converting information related to an area ratio u of a rectangular writing pattern, factor amount converting information related to an opening angle Ω of a recessed writing pattern, factor amount converting information related to an area ratio u of a recessed writing pattern, or the like.

The factor amount converting information may be, for example, a pair of the high-fidelity information that is a numerical value and the low-fidelity information that is a numerical value. The pair of the high-fidelity information that is a numerical value and the low-fidelity information that is a numerical value may be, for example, a set of pairs (α, ß) each consisting of a numerical value a corresponding to the low-fidelity information and a numerical value ß corresponding to the high-fidelity information as shown in FIG. 3.

FIG. 3 is a table showing an example of factor amount converting information constituted by a set of pairs of numerical values. The factor amount converting information is factor amount converting information related to a specific factor amount, of a specific writing pattern. The specific writing pattern is, for example, a rectangular writing pattern, but also may be a writing pattern in the shape other than a rectangle, such as a recessed shape, a projecting shape, a stepped shape, or the like. The specific factor amount is, for example, a numerical value group of the opening angle Ω, but also may be a numerical value group of the area ratio u or the like.

The set of numerical value pairs (α, ß) may be specifically, for example, (0, 0), (0.110973, 0.09414), (0.218646, 0.183325), . . . , and (1, 1), or the like. Note that the total number of pairs constituting the factor amount converting information, specific numerical values or each pair, and the like described above are merely an example, and may be variously changed according to a combination of a writing pattern and factors.

Alternatively, the factor amount converting information may be, for example, a function in which the low-fidelity information is taken as input and the high-fidelity information is taken as output. The function is, for example, a polynomial function, a spline function, or the like, but there is no limitation on its type.

The polynomial function may be represented, for example, as a formula shown in Numerical Formula 2.

$$y = ax^3 + bx^2 + cx \qquad \text{Numerical Formula 2}$$

In Numerical Formula 2, the coefficients of the first to third terms may be, for example, a=−1, 2912, b=1.9071, and c=0.3704. Note that there is no limitation on the number of terms or the coefficients of the polynomial formula.

The spline function may be represented, for example, as a formula shown in Numerical Formula 3.

$$s(t) = \sum_{i=0}^{m-n-2} p_i b_{i,n}(t) \qquad \text{Numerical Formula 3}$$

$$b_{i,0}(t) = \begin{cases} 1 & (t_i \le t < t_{i+1}) \\ 0 & (\text{otherwise}) \end{cases}$$

$$b_{i,n}(t) =$$

$$\frac{t - t_i}{t_{i+n} - t_i} b_{i,n-1}(t) + \frac{t_{i+n+1} - t}{t_{i+n+1} - t_{i+1}} b_{i+1,n-1}(t)$$

In Numerical Formula 3, $t_i$ is a value of a an $i^{-th}$ knot among m knots, and $P_i$ is a coefficient that is paired with $t_i$. A set pairs $(t_i, P_i)$ each consisting of knot and a coefficient may be, for example, as shown in FIG. 4.

FIG. 4 is a table showing an example of a set of pairs each consisting of a knot and a coefficient in a spline function. In this example, m=29, and the set of pairs each consisting of a knot and a coefficient includes a pair of a first knot "0" and a coefficient "0.0001038443", a pair of a second knot "0" and a coefficient "0.0001038443" . . . , and a pair of a $29^{-th}$ knot "1" and a coefficient "0.9998961557", or the like.

Note that the factor amount converting information may be represented as a function other than a polynomial function or a spline function, and there is no limitation on its representing format. Also, there is no limitation on the data structure of the factor amount converting information constituted by a pair of numerical values.

In the factor amount converting information storage unit 111, these sorts of two or more pieces of factor amount converting information may be stored in association with a shape identifier. The state of being stored in association with a shape identifier also includes a case in which the factor amount converting information has the shape identifier. The shape identifier is information for identifying a shape of a writing pattern. The shape identifier may be, for example, "rectangular shape (three sides)", "recessed shape", "projecting shape", "stepped shape", or the like, or may be IDs or the like associated therewith. The various shapes will be described later.

In the factor amount converting information storage unit 111, these sorts of two or more pieces of factor amount converting information may be stored in association with a pair of a shape identifier and a factor identifier. The factor identifier is information for identifying a factor. The factor identifier may be, for example, "opening angle Ω", "area ratio u", or the like, or may be IDs or the like associated therewith.

In the writing pattern information storage unit 112, one or at least two pieces of writing pattern information are stored. The writing pattern information is information related to a writing pattern. The writing pattern is an element constituting a figure that is to be written, and may also be said to be an element having various shapes. The writing pattern may be defined by, for example, one or at least two sides. A figure such as an electronic circuit that is to be written on a photomask may be written, for example, by combining various writing patterns defined by one or at least two sides as shown in FIG. 5.

Figure 5:
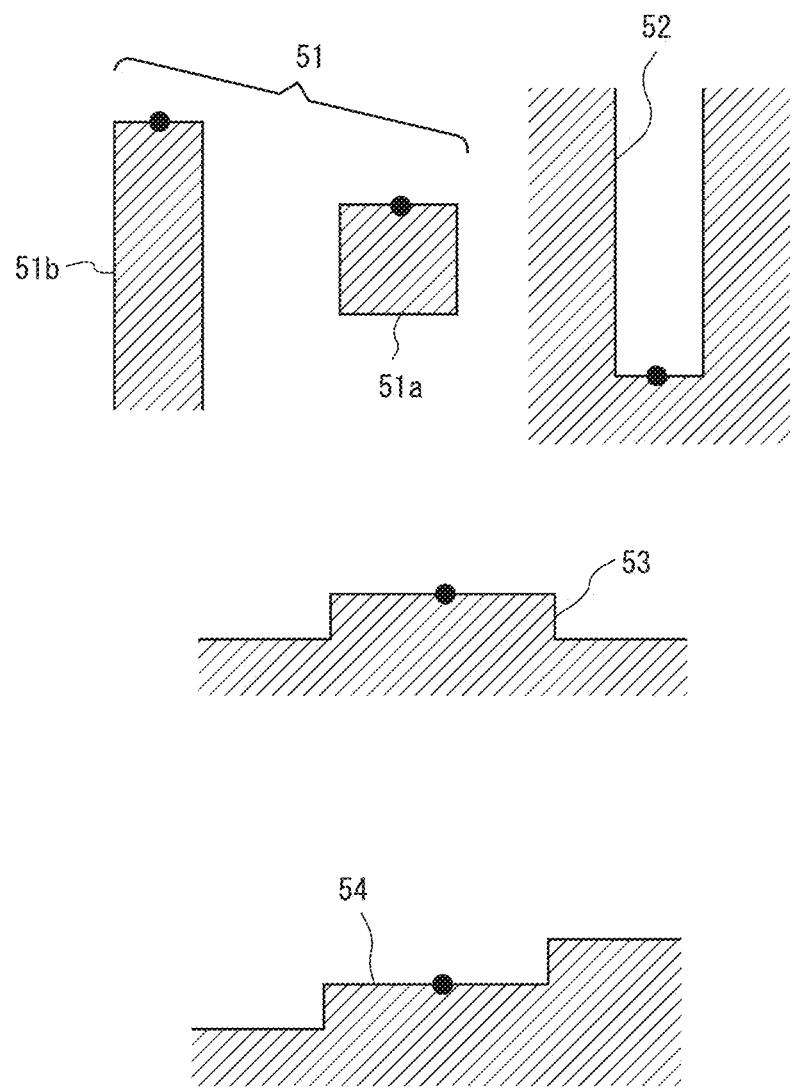
FIG. 5 is a diagram showing various writing patterns in the embodiment.

FIG. 5 is a diagram showing various writing patterns. The various writing patterns may be, for example, rectangular writing patterns 51, a recessed writing pattern 52, a projecting writing pattern 53, a stepped writing pattern 54, or the like.

There may be two types of the rectangular writing patterns 51 consisting of, for example, a writing pattern 51a defined by four sides corresponding to a contour line of a closed rectangle, and a writing pattern 51b defined by three of the four sides. The one side that is the remaining one of the four sides, and that does not constitute the writing pattern 52b is a portion that is connected to another writing pattern and, typically, that is not written.

Furthermore, the recessed writing pattern 52 is, for example, a writing pattern defined by three sides corresponding to a recess of a polygon. The projecting writing pattern 53 is, for example, a writing pattern defined by five sides corresponding to a projection of a polygon. The stepped writing pattern 54 is, for example, a writing pattern defined by five sides corresponding to steps of a polygon. In addition to the writing patterns shown in the drawing, for example, there may be a writing pattern defined by only one side, a writing pattern defined by two sides corresponding to an edge of a polygon, and the like.

Each of the circles attached to the various writing patterns in FIG. 5 indicates one evaluation point that is arranged on one side constituting the writing pattern. Although not shown, it is preferable that one evaluation point is arranged on the other sides.

It is preferable that, in the writing pattern information storage unit 112, two or more pieces of writing pattern information indicating these sorts of various writing patterns are stored. If two or more pieces of writing pattern information are stored, for example, the above-described shape identifier such as "rectangular shape (three sides)", "recessed shape", or the like is associated with each piece of writing pattern information. The state of being stored in association with a shape identifier also includes a case in which the writing pattern information has the shape identifier.

The accepting unit 12 accepts various types of information. The various types of information are, for example, image data of a figure that is to be formed through etching, writing pattern information, various instructions, or the like. The various instructions are, for example, a factor amount converting information configuring instruction, a simulation result outputting instruction, a correction result outputting instruction, or the like. These instructions will be described later. The accepting is a concept that encompasses accepting information input from an input device such as a keyboard, a mouse, or a touch panel, receiving information transmitted via a network, a communication line, or the like, accepting information read from a storage medium such as a disk or a semiconductor memory, and the like.

Specifically, the accepting unit 12 accepts image data of a figure that is to be formed through etching, for example, from a mouse, a touch panel, or the like, in a hand-written mode, but it is also possible that the data is read from a storage medium, or received via a network or the like. The accepting unit 12 accepts one or more pieces of writing pattern information used for a simulation, for example, through reading from a storage medium, or receiving via a network, but it is also possible that the information is accepted via a mouse or the like in a hand-written mode. It is also possible that the accepting unit 12 accepts various instructions, for example, via an input device such as a keyboard.

The processing unit 13 performs various types of processing. The various types of processing are, for example, the above-described simulations, and are, specifically, processes by the ADI simulation unit 131, the converting unit 132, the etching simulation unit 133, the shape identifier acquiring unit 134, or the like.

Furthermore, it is preferable that, for example, upon the accepting unit 12 accepting image data, the processing unit 13 repeats processing for selecting, for that image data, one piece of writing pattern information from among the one or more writing patterns stored in the writing pattern information storage unit 112, specifying one or more portions that match the image pattern, performing a simulation for each portion, and acquiring a function indicating a line width change in an etch contour in each portion, until there is no more writing pattern information that has not been selected, thereby acquiring a function group for the image data.

Furthermore, it is possible that, for example, upon the accepting unit 12 accepting factor amount converting information configuring instruction, the processing unit 13 configures factor amount converting information for each of the one or more pieces of writing pattern information stored in the writing pattern information storage unit 112, and accumulates it in the factor amount converting information storage unit 111. The factor amount converting information configuring instruction is an instruction to configure factor amount converting information.

Specifically, it is preferable that, for example, the processing unit 13 repeats processing for selecting one piece of writing pattern information from among the one or more pieces of writing pattern information stored in the writing pattern information storage unit 112, causing the ADI simulation unit 131 to perform an ADI simulation using the first number of evaluation points, on the one piece of writing pattern information, and, furthermore, causing the ADI simulation unit 131 to perform an ADI simulation using the second number of evaluation points, the second number being larger than the first number, configuring factor amount converting information using a pair of low-fidelity information, which is one or more factor amounts acquired through the former ADI simulation, and high-fidelity information, which is one or more factor amounts acquired through the latter ADI simulation, and accumulating the configured factor amount converting information in the factor amount converting information storage unit 111 in association with the writing pattern information, until there is no more writing pattern information that has not been selected. The state of being in association with writing pattern information may be a state in which, for example, factor amount converting information is in association with a shape identifier for identifying a shape of a writing pattern indicated by the writing pattern information.

Note that it is possible that, for example, each time the accepting unit 12 accepts writing pattern information, the processing unit 13 configures factor amount converting information for the writing pattern information.

Alternatively, instead of the processing unit 13 configuring factor amount converting information, one or more pieces of factor amount converting information configured by another processing apparatus may be stored in advance in the factor amount converting information storage unit 111.

The ADI simulation unit 131 performs an ADI simulation using one or more evaluation points, on a writing pattern indicated by the writing pattern information, thereby acquiring one or more factor amounts.

For example, it is also possible that the ADI simulation unit 131 arranges one or more evaluation points on the outer periphery of a writing pattern indicated by the writing pattern information, performs a model-based ADI simulation, moves the one or more evaluation points to a position satisfying a predetermined condition, and acquires one or more factor amounts at each of the one or more evaluation points after movement. The arranging one or more evaluation points may be, for example, setting coordinate values indicating a position of each of the one or more points on the outer periphery of a writing pattern, as initial coordinate values indicating a position of each of the one or more evaluation points. The moving the one or more evaluation points may be changing the coordinate values initially set for each of the one or more evaluation points, to coordinate values satisfying a predetermined condition. Numerical Formulas 4 to 6 shown later may also be said to be an example of numerical formula group indicating this condition.

In this example, the arranging one or more evaluation points on the outer periphery of a writing pattern may be, for example, arranging one evaluation point on each of the one or more sides constituting the writing pattern. Note that the number of evaluation points that are arranged on each of the one or more sides also may be two or more.

The model-based ADI simulation may include, for example, acquiring a resist contour through a threshold model as described above. The threshold model is a model for acquiring a contour line of resist after development through a comparison between an amount of energy accumulated at one or more evaluation points and a threshold.

If the amount of energy given, when electron beams are incident on one point, to the vicinity of that point is represented by a distribution function $p(r)$, an accumulated energy distribution $E(x)$ that appears, when electron beam irradiation is performed in order to write a pattern with a given shape, in the vicinity of that pattern can be acquired through convolution, for example, using Numerical Formula 4.

$$E(x) = \int_{pattern} p(x'-x) dx' \quad \text{Numerical Formula 4}$$

As the distribution function $p(r)$, for example, a double Gaussian function of Numerical Formula 5 may be used.

$$p(r) = \frac{1}{\pi(1+\eta)} \left( \frac{1}{\sigma_a^2} \exp\left(-\frac{r^2}{\sigma_a^2}\right) + \frac{\eta}{\sigma_b^2} \exp\left(-\frac{r^2}{\sigma_b^2}\right) \right) \quad \text{Numerical Formula 5}$$

In the formula, $\sigma_a$ is a forward scattering radius, $\sigma_b$ is a backward scattering radius, and $\eta$ is an intensity ratio between forward scattering and backward scattering.

The threshold model is a model for acquiring a resist contour, which is a boundary between a region in which the resist dissolves and a region in which the resist does not dissolve, for example, through processing in which the resist is regarded as dissolving at a point where the accumulated energy $E(x)$ acquired using Numerical Formula 4 is greater than the threshold Eth or is greater than or equal to the threshold, and is regarded as not dissolving at a point where the accumulated energy $E(x)$ is less than or equal to the threshold Eth or is less than the threshold. Accordingly, a set of points x at which it can be regarded as $E(x)=Eth$, with respect to the accumulated energy distribution $E(x)$ acquired using Numerical Formula 4, forms a resist contour.

Figure 6:
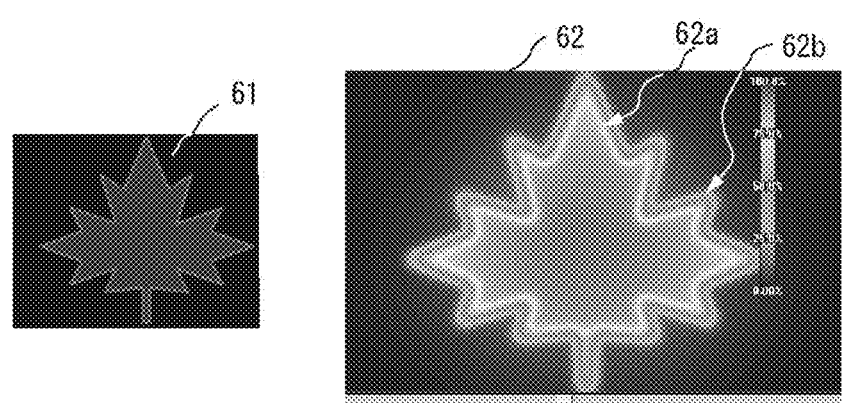
FIG. 6 is a diagram showing an example of accumulated energy distribution acquired for a certain writing pattern in the embodiment.

FIG. 6 is a diagram showing an example of accumulated energy distribution acquired using Numerical Formula 3 and the like, through beam irradiation corresponding to a certain writing pattern. A writing pattern 61 indicates a shape of beam irradiation, and a color temperature pattern 62 indicates accumulated energy distribution. In the color temperature pattern 62, portions with the same color (e.g., a yellow portion 62a, a green portion 62b, etc.) are portions at which the same amount of energy has accumulated, and are portions that may form a resist contour. Which color of a portion corresponds to a portion that forms a resist contour depends on the threshold Eth. For example, if the range in which it can be regarded as $E(x)=Eth$, with respect to a predetermined threshold Eth, is the yellow portion 62a, the yellow portion 62a forms a resist contour.

The resist contour based on the predetermined threshold Eth is, for example, a set of points x satisfying Numerical Formula 6.

$$\int_{pattern} p(x'-x) dx' = E_{th} \quad \text{Numerical Formula 6}$$

However, it is not possible to explicitly solve Numerical Formula 6. Thus, the ADI simulation unit 131 arranges one or more evaluation points on the outer periphery of the writing pattern 61, and, until an accumulated energy $E(x)$ for each of the one or more evaluation points becomes close to a predetermined threshold Eth enough to be regarded as being equal to the threshold, repeats processing for calculating the accumulated energy $E(x)$, and moving each evaluation point to the outer side of the outer periphery in a case in which the accumulated energy $E(x)$ is greater than the threshold Eth or moving the evaluation point to the inner side of the outer periphery in a case in which the accumulated energy $E(x)$ is less than the threshold Eth. The ADI simulation unit 131 acquires, as a resist contour, a set of one or more evaluation points after movement to realize $E(x)=Eth$. Whether or not the accumulated energy $E(x)$ is close to the threshold Eth enough to be regarded as being equal to the threshold can be judged, for example, based on whether or not a difference $\Delta E$ between the accumulated energy $E(x)$ and the threshold Eth is less than, or is less than or equal to a predetermined another threshold $\Delta Eth$. The moving an evaluation point to the outer side of the outer periphery may be, for example, changing coordinate values of the evaluation point such that the evaluation point moves by a predetermined distance away from a center point of the outer periphery (e.g., the center of gravity of a rectangle) along a normal direction of the outer periphery or substantially the normal direction. In a similar manner, the moving an evaluation point to the inner side of the outer periphery may be, for example, changing coordinate values of the evaluation point such that the evaluation point moves by a predetermined distance closer to a center point of the outer periphery along a normal direction of the outer periphery or substantially the normal direction. Note that there is no limitation on the method in which the ADI simulation unit 131 judges whether or not the accumulated energy $E(x)$ is close to the threshold Eth enough to be regarded as being equal to the threshold. Also, there is no limitation on the manner in which the ADI simulation unit 131 moves an evaluation point to the outer side or to the inner side of the outer periphery.

Note that an edge portion of a resist contour is typically rounded, for example, as indicated by the resist contour (e.g., the yellow portion 62a) shown in FIG. 6. Accordingly, in order to acquire an edge contour with a high level of accuracy that makes it possible to represent even a rounded shape of an edge portion, it is necessary for the ADI simulation unit 131 to perform the above-described threshold model-based ADI simulation, for example, using a large number of evaluation points such as 10 or plus to several tens of evaluation points, for each of the one or more writing patterns constituting a figure, and thus the simulation speed decreases.

Furthermore, for example, the ADI simulation unit 131 acquire one or more factor amounts such as the opening angle Ω and the area ratio u described above, at each of the one or more evaluation points after movement to realize E(x)=Eth, during the above-described threshold model-based ADI simulation.

For example, it is also possible that the ADI simulation unit 131 arranges one or more evaluation points again along the resist contour acquired through the threshold model-based ADI simulation, and acquires one or more factor amounts at each of the one or more evaluation points.

In order to obtain a simulation result with a high level of accuracy in the following etching simulation, it is necessary to acquire high-fidelity information, which is one or more factor amounts with a high level of precision acquired using a large number of evaluation points, through an ADI simulation. However, it is necessary to perform a large amount of calculation also for this processing, and thus the ADI simulation speed further decreases.

Thus, for example, the ADI simulation unit 131 arranges the first number of evaluation points on the outer periphery of a writing pattern indicated by one piece of writing pattern information, performs a threshold model-based ADI simulation, moves each of the one or more evaluation points to a position at which the accumulated energy E(x) at the evaluation point can be regarded as being equal to the threshold Eth, and acquires one or more factor amounts such as the opening angle Q and the area ratio u at each of the one or more evaluation points after movement.

It is preferable that the first number is, for example, the same as the number of sides constituting the writing pattern. Note that the first number may be larger than the number of sides constituting the writing pattern, and may be, for example, a number that is obtained by multiplying the number of sides constituting the writing pattern by a natural number (by one, two, etc.).

That is to say for example, it is preferable that the ADI simulation unit 131 in particular arranges one evaluation point on each of the N sides constituting a writing pattern indicated by one piece of writing pattern information, performs a threshold model-based ADI simulation, moves each of the N evaluation points to a position at which the accumulated energy E(x) at the evaluation point can be regarded as being equal to the threshold Eth, and acquires one or more factor amounts such as the opening angle Ω and the area ratio u at each of the N evaluation points after movement.

Note that it is also possible that, for example, the ADI simulation unit 131 arranges M evaluation points (M is a natural number of two or more) on each of the N sides constituting a writing pattern indicated by one piece of writing pattern information, performs a threshold model-based ADI simulation, moves each of the N×M evaluation points to a position at which the accumulated energy E(x) at the evaluation point can be regarded as being equal to the threshold Eth, and acquires one or more factor amounts such as the opening angle 9 and the area ratio u at each of the N×N evaluation points after movement. The number of evaluation points that are arranged at the sides may not be the same.

For example, it is more preferable that, when the processing unit 13 generates factor amount converting information corresponding to the one or more pieces of writing pattern information stored in the writing pattern information storage unit 112, the ADI simulation unit 131 first performs an ADI simulation as described above using the first number of evaluation points, on a writing pattern indicated by the writing pattern information, thereby acquiring low-fidelity information, which is one or more factor amounts with a low level of precision, and, furthermore, performs an ADI simulation again using the second number of evaluation points, the second number being larger than the first number, thereby acquiring high-fidelity information, which is one or more factor amounts with a high level of precision.

The converting unit 132 converts the low-fidelity information to the high-fidelity information, using the factor amount converting information. Specifically, the converting unit 132 acquires high-fidelity information using the factor amount converting information stored in the factor amount converting information storage unit 111, wherein the high-fidelity information corresponds to the low-fidelity information, which is one or more factor amounts acquired by the ADI simulation unit 131 using the first number of evaluation points for one piece of writing pattern information, and the high-fidelity information is one or more factor amounts acquired using the second number of evaluation points, the second number being larger than the first number.

For example, it is preferable that, if two or more pieces of factor amount converting information are stored in association with a shape identifier (e.g., "rectangular shape (three sides)", "recessed shape", etc.) in the factor amount converting information storage unit 111, the converting unit 132 acquires high-fidelity information corresponding to the low-fidelity information, using factor amount converting information corresponding to the writing pattern information, among the two or more pieces of factor amount converting information. In this example, the factor amount converting information corresponding to the writing pattern information may be, for example, factor amount converting information corresponding to the shape identifier acquired by the later-described shape identifier acquiring unit 134.

Furthermore, for example, it is more preferable that, if two or more pieces of factor amount converting information are stored in association with a pair of a shape identifier and a factor (e.g., a pair of "rectangular shape (three sides)" and "opening angle Ω", a pair of "recessed shape" and "area ratio u", etc.) in the factor amount converting information storage unit 111, the converting unit 132 acquires high-fidelity information corresponding to the low-fidelity information, using factor amount converting information corresponding to the pair of the shape identifier corresponding to the writing pattern information and the factor identifier corresponding to the low-fidelity information, among the two or more pieces of factor amount converting information.

If the factor amount converting information stored in the factor amount converting information storage unit 111 is, for example, a pair of the low-fidelity information that is a numerical value and the high-fidelity information that is a numerical value, the converting unit 132 acquires low-fidelity information, which is the one or more factor amounts acquired by the ADI simulation unit 131, the low-fidelity information being a numerical value that is paired with the low-fidelity information that is a numerical value.

Furthermore, if the stored factor amount converting information is, for example, a function in which the low-fidelity information is taken as input and the high-fidelity information is taken as output, the converting unit 132 may input the acquired low-fidelity information to the function, thereby acquiring high-fidelity information. The function is, for example, the polynomial function of Numerical Formula 2, the spline function of Numerical Formula 3, or the like, but there is no limitation on its type.

The etching simulation unit 133 performs an etching simulation basically using the one or more factor amounts acquired by the ADI simulation unit 131. That is to say, the etching simulation unit 133 performs an etching simulation as described above, for example, using the one or more factor amounts acquired by the ADI simulation unit 131 at each of the one or more evaluation points after movement as described above, thereby acquiring an etch contour.

Furthermore, the etching simulation unit 133 may also acquire a function $\delta = f(\Omega, u)$ indicating the line width change $\delta$ in the etch contour, for each of the one or more evaluation points after movement by the ADI simulation unit 131.

Figure 7:
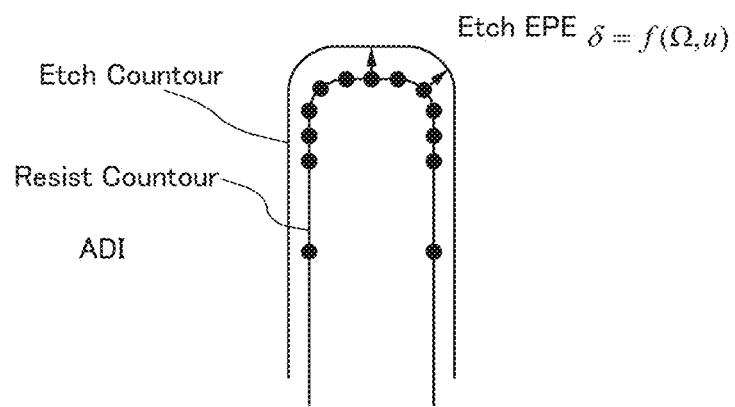
FIG. 7 is a conceptual diagram showing a line width change δ in an etch contour at each of the one or more evaluation points after movement in an ADI simulation in the embodiment.

FIG. 7 is a conceptual diagram showing a line width change $\delta$ in an etch contour at each of the one or more evaluation points after movement in an ADI simulation. In this example, 13 evaluation points are located along a resist contour. The 13 evaluation points correspond to the 13 evaluation points after movement by the ADI simulation unit 131. In other words, the line extending along the 13 evaluation points after movement by the ADI simulation unit 131 represent a resist contour. Among the 13 evaluation points along the resist contour, line width changes $\delta$ at evaluation points at the seventh and ninth order from the left are indicated by two arrows in the drawing. A line width change $\delta$ may be considered as a vector represented as a function $\delta = f(\Omega, u)$ in which the opening angle $\Omega$ and the area ratio u acquired at each of the evaluation points are taken as parameters.

For example, for each of the one or more evaluation points after movement by the ADI simulation unit 131, the etching simulation unit 133 may substitute the opening angle $\Omega$ and the area ratio u acquired at the evaluation point for the function $\delta = f(\Omega, u)$, thereby acquiring a vector indicating the line width change $\delta$, and add the vector. The etching simulation unit 133 can acquire an etch contour by acquiring a line extending along one or more evaluation points after the addition.

Furthermore, it is possible for the etching simulation unit 133 to perform an etching simulation accurately at high speed, in particular using the one or more factor amounts acquired by the converting unit 132. That is to say, for example, the etching simulation unit 133 may acquire this sort of function by performing an etching simulation, using the one or more factor amounts that are high-fidelity information, which is one or more factor amounts acquired by the converting unit 132 using the factor amount converting information on low-fidelity information, which is one or more factor amounts acquired by the ADI simulation unit 131 using the first number of evaluation points, the one or more factor amounts being acquired using the second number of evaluation points, the second number being larger than the first number.

the shape identifier acquiring unit 134 acquires a shape identifier for identifying a shape of a writing pattern that is specified with the writing pattern information.

For example, it is sufficient that such a shape identifier is associated with each of the one or more pieces of writing pattern information stored in the writing pattern information storage unit 112, and the shape identifier acquiring unit 134 acquires a shape identifier corresponding to the writing pattern information subjected to writing.

The judging unit 135 acquires residuals respectively at evaluation points, using a result of the etching simulation obtained by the etching simulation unit 133. The etching simulation result is, for example, an etch contour, but also may be a line width change. The residual is difference between an etch contour, which is an etching simulation result, and a resist contour, which is an ADI simulation result, and is also referred to as an edge placement error. The residual may be represented, for example, as a function indicating a line width change in an etch contour.

Furthermore, the judging unit 135 judges whether or not an error is small enough to satisfy a predetermined condition, using the thus acquired one or more residuals. A residual is a difference between an etch contour, which is an etching simulation result, and a resist contour, which is an ADI simulation result, whereas an error may also be said to be a difference between such an etch contour and a contour of an original writing pattern.

The judging unit 135 may acquire an error, for example, by subtracting a positional vector at each of the one or more original evaluation points before movement, from an result obtained by adding a vector indicating the line width change $\delta$ acquired using the function $\delta = f(\Omega, u)$, for each of the one or more evaluation points after movement by the ADI simulation unit 131. The predetermined condition may be, for example, a condition that the thus acquired error is less than or is less than or equal to the predetermined threshold.

If the judging unit 135 judges that the predetermined condition is not satisfied, the pattern information changing unit 136 changes the writing pattern information, using a function group indicating residuals of the one or more evaluation points. The changing the writing pattern information using a residual may be, for example, changing the writing pattern information once or at least twice such that the one or more of a residual and an error acquired using the residual become close to 0. The changing the writing pattern information may be, for example, changing the initial coordinate values indicating a position of each of the one or more original evaluation points before movement by the ADI simulation unit 131. Accordingly, it is possible to obtain a writing pattern in which an error is corrected to 0.

The output unit 14 outputs various types of information. The various types of information are, for example, an image of a figure that is to be formed through etching, a simulation result obtained by the processing unit 13 or the like, image pattern information after change by the pattern information changing unit 136, or the like. The output unit 14 typically outputs information such as an image of a figure or a simulation result via an output device such as a display screen or a speaker, but may output information, for example, through printing by a printer, accumulation in a storage medium, or transmission to an external apparatus.

For example, upon the accepting unit 12 accepting image data, the output unit 14 may configure one or more of the image of a writing pattern after etching and the image of a writing pattern after development corresponding to the image data, using a function group acquired by the processing unit 13 or the like performing a simulation, and display the one or more images on a display screen.

It is preferable that, for example, the output unit 14 displays a writing pattern after etching configured by the etching simulation unit 133 using the function group, in a first mode (e.g., red, solid line, etc.), and further displays an accepted original writing pattern corresponding to image data, in a second mode (e.g., green, dotted line, etc.).

Furthermore, it is more preferable that the output unit 14 displays a resist contour acquired using an evaluation point group after movement by the ADI simulation unit 131, in a third mode (e.g., blue, dashed dotted line, etc.).

The output unit 14 may output a simulation result, for example, according to a simulation result outputting instruction, and there is no limitation on a trigger to perform the output. The simulation result outputting instruction is an instruction to output a simulation result.

Furthermore, for example, the output unit 14 may output the writing pattern information after change by the pattern information changing unit 136, according to a correction result outputting instruction. The correction result outputting instruction is an instruction to output a correction result. The correction result is writing pattern information after change, and also may be an image of a writing pattern that has been corrected based on the writing pattern information after change. There is no limitation on a trigger to output the correction result.

Alternatively, for example, the output unit 14 may output a moving image of the writing pattern that is being corrected, using the writing pattern information during change by the pattern information changing unit.

The storage unit 11, the factor amount converting information storage unit 111, and the writing pattern information storage unit 112 are, are preferably non-volatile storage media such as a hard disk or a flash memory, but may be realized also by volatile storage media such as a RAM.

There is no limitation on the procedure in which information is stored in the storage unit 11 and the like. For example, information may be stored in the storage unit 11 and the like via a storage medium, information transmitted via a network, a communication line, or the like may be stored in the storage unit 11 and the like, or information input via an input device may be stored in the storage unit 11 and the like. The input device may be any device, for example, such as a keyboard, a mouse, a touch panel, or the like.

The accepting unit 12 may be considered to include or to not include an input device. The accepting unit 12 may be realized by driver software for an input device, a combination of driver software for an input device and the input device, or the like.

The processing unit 13, the ADI simulation unit 131, the converting unit 132, the etching simulation unit 133, the shape identifier acquiring unit 134, the judging unit 135, and the pattern information changing unit 136 may be realized typically by MPUs, memories, or the like. Typically, the processing procedure of the processing unit 13 and the like is realized by software, and the software is stored in a storage medium such as a ROM. Note that the processing procedure may be realized also by hardware (dedicated circuits).

The output unit 14 may be considered to include or to not include an output device such as a display screen or a speaker. The output unit 14 may be realized by driver software for an output device, a combination of driver software for an output device and the output device, or the like.

Next, an operation of the simulation apparatus 1 will be described with reference to the flowcharts in FIGS. 8 and 9.

Figure 8:
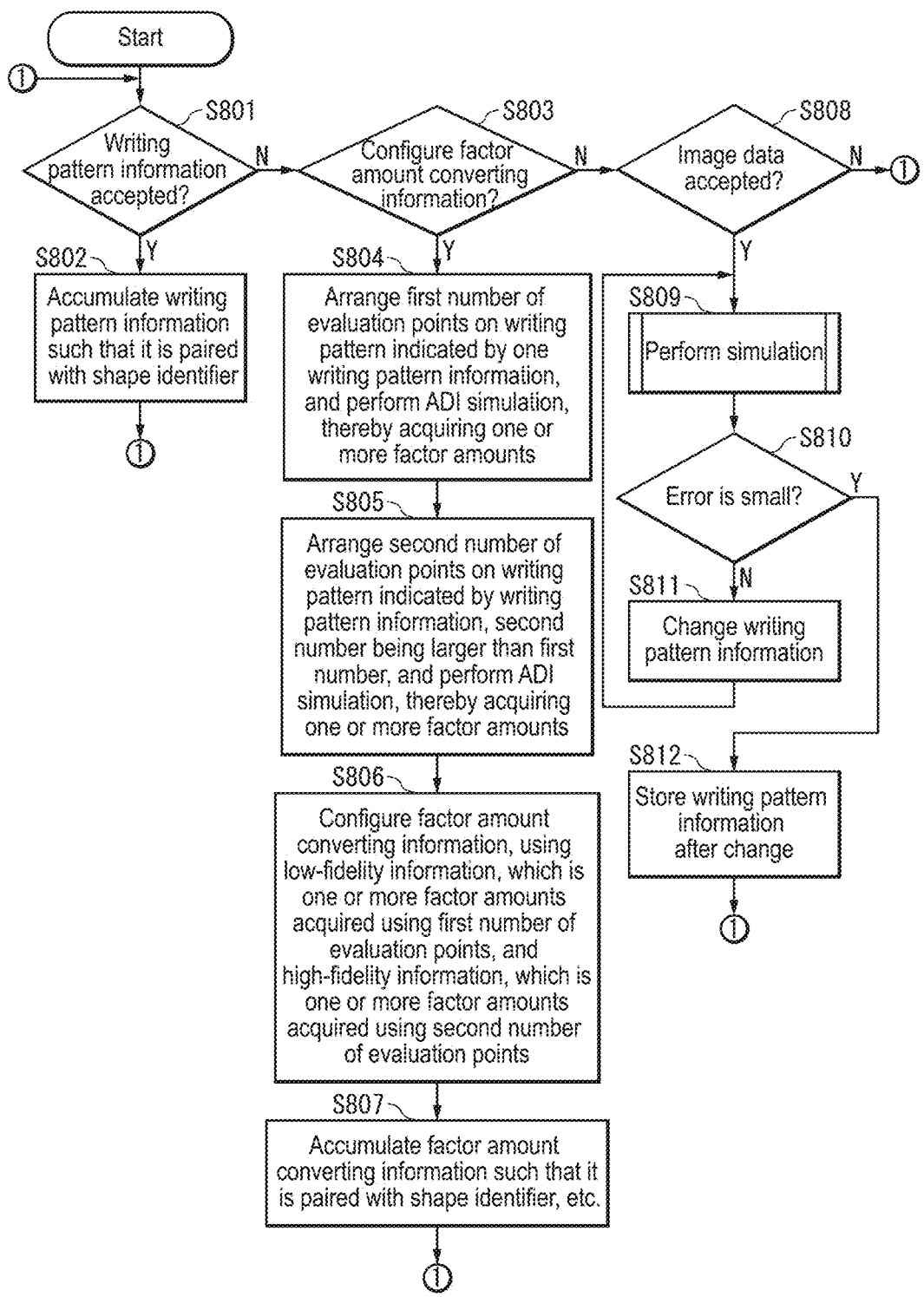
FIG. 8 is a flowchart illustrating an operation of the simulation apparatus in the embodiment.

FIG. 8 is a flowchart illustrating an operation of the simulation apparatus 1.

(Step S801) The processing unit 13 judges whether or not the accepting unit 12 has accepted writing pattern information. If the accepting unit 12 has accepted writing pattern information, the procedure advances to step S802, and, if not, the procedure advances to step S803.

(Step S802) The processing unit 13 accumulates the accepted writing pattern information in the writing pattern information storage unit 112 such that it is paired with a shape identifier for identifying a shape of a writing pattern indicated by the writing pattern information. Then, the procedure returns to step S801.

(Step S803) The processing unit 13 judges whether or not to configure factor amount converting information. Specifically, for example, the processing unit 13 may judge to configure factor amount converting information if it is judged in step S801 that the accepting unit 12 has accepted writing pattern information or if the writing pattern information is accumulated in step S803. Alternatively, for example, the processing unit 13 may judge to configure factor amount converting information if the accepting unit 12 has accepted factor amount converting information configuring instruction, and there is no limitation on a trigger to configure factor amount converting information.

If factor amount converting information is to be configure, the procedure advances to step S804, and, if not, the procedure advances to step S808.

(Step S804) The ADI simulation unit 131 arrange the first number of evaluation points on the writing pattern indicated by one piece of writing pattern information, and performs an ADI simulation, thereby acquiring one or more factor amounts. The ADI simulation will be described with reference to the flowchart in FIG. 10. The one piece of writing pattern information may be, for example, the writing pattern information accepted in step S801, or may be the writing pattern information selected from the writing pattern information storage unit 112.

(Step S805) The ADI simulation unit 131 arranges the second number of evaluation points on the writing pattern indicated by the writing pattern information, the second number being larger than the first number, and performs an ADI simulation, thereby acquiring one or more factor amounts. The ADI simulation will be described with reference to the flowchart in FIG. 10.

(Step S806) The processing unit 13 configures factor amount converting information corresponding to the writing pattern information, using low-fidelity information, which is one or more factor amounts acquired in step S804 using the first number of evaluation points, and high-fidelity information, which is one or more factor amounts acquired in step S805 using the second number of evaluation points.

(Step S807) The processing unit 13 accumulates the factor amount converting information configured in step S807 in the factor amount converting information storage unit 111 such that it is paired with a shape identifier corresponding to the writing pattern information or is paired with a pair of a shape identifier corresponding to the writing pattern information and a factor identifier corresponding to the factor amount acquired in step S804 or the like. Then, the procedure returns to step S801.

(Step S808) The processing unit 13 judges whether or not the accepting unit 12 has accepted image data. If the accepting unit 12 has accepted image data, the procedure advances to step S809, and, if not, the procedure returns to step S801.

(Step S809) The processing unit 13 and the like perform a simulation for the accepted image data. The simulation will be described with reference to the flowchart in FIG. 9.

(Step S810) The judging unit 135 acquires one or more residuals using a function group, which is a line width change acquired by the etching simulation unit 133, in the simulation in step S809, and judges whether or not an error is small enough to satisfy a predetermined condition, using the acquired one or more residuals. If an error is small enough to satisfy a predetermined condition, the procedure advances to step S812, and, if not, the procedure returns to step S809.

(Step S811) The pattern information changing unit 136 changes the writing pattern information, using the function group. Then, the procedure returns to step S089.

(Step S812) The processing unit 13 stores the writing pattern information after change in step S811 in the storage unit 11 or the like in association with the original writing pattern information. Then, the procedure returns to step S801.

Furthermore, in the flowchart in FIG. 8, the procedure is started at turning on of the simulation apparatus 1 or start of the program, and is terminated at turning off or an interruption at the end of the process. Note that there is no limitation on a trigger to start or end the process.

Figure 9:
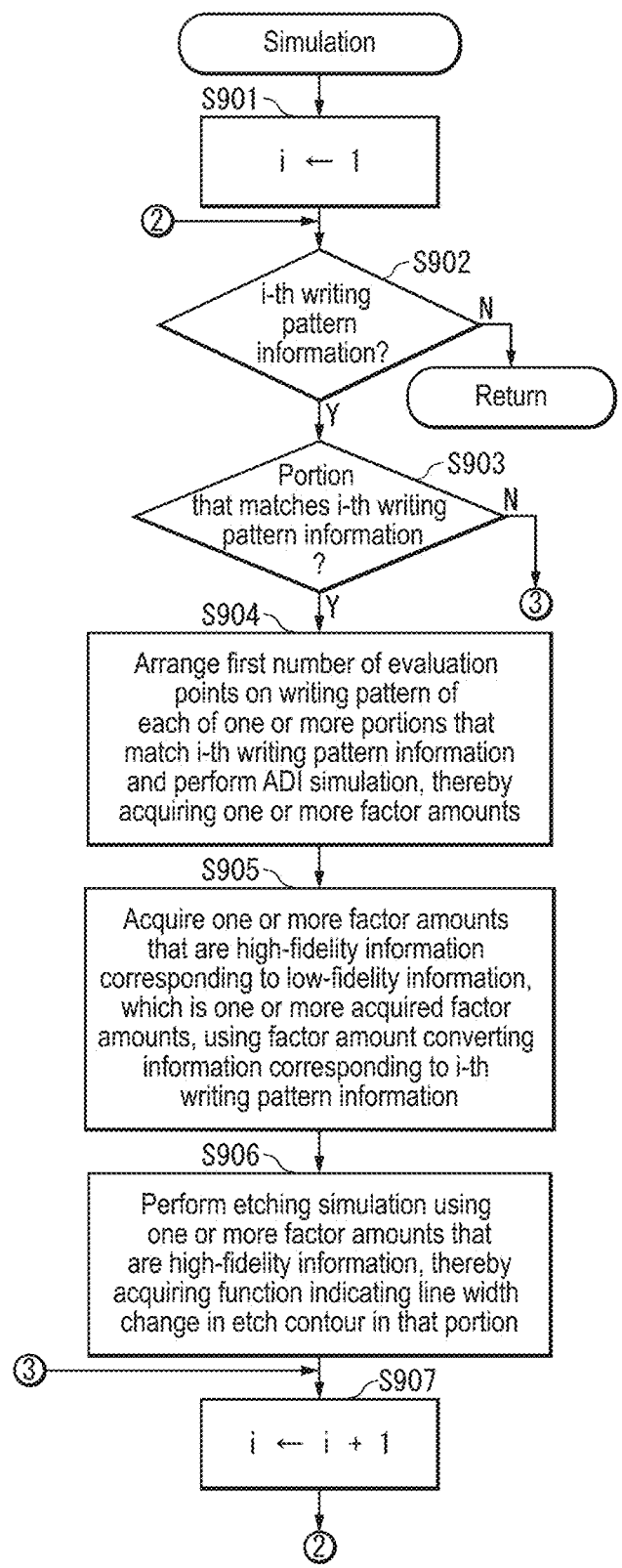
FIG. 9 is a flowchart illustrating a simulation in the embodiment.

FIG. 9 is a flowchart illustrating a simulation in step S809 described above.

(Step S901) The processing unit 13 sets an initial value 1 to a variable i. The variable i is a variable for sequentially selecting those that have not been selected, among the one or more pieces of writing pattern information stored in the writing pattern information storage unit 112.

(Step S902) The processing unit 13 judges whether or not there is an $i^{-th}$ piece of writing pattern information. If there is an $i^{-th}$ piece of writing pattern information, the procedure advances to step S903, and, if not, the procedure returns to the upper-level processing.

(Step S903) The processing unit 13 judges whether or not the accepted image data has a portion that matches the $i^{-th}$ piece of writing pattern information. If the image data has a portion that matches the $i^{-th}$ piece of writing pattern information, the procedure advances to step S903, and, if not, the procedure advances to step S907.

(Step S904) The ADI simulation unit 131 arranges the first number of evaluation points on the writing pattern of each of the one or more portions that match the $i^{-th}$ piece of writing pattern information and performs an ADI simulation, thereby acquiring one or more factor amounts. The ADI simulation will be described with reference to the flowchart in FIG. 10.

(Step S905) The converting unit 132 acquire one or more factor amounts that are high-fidelity information corresponding to the low-fidelity information, which is one or more factor amounts acquired in step S904, using factor amount converting information corresponding to the $i^{-th}$ piece of writing pattern information.

(Step S906) The etching simulation unit 133 performs an etching simulation using the one or more factor amounts that are high-fidelity information acquired in step S905, thereby acquiring a function indicating a line width change in an etch contour in that portion.

(Step S907) The processing unit 13 increments the variable i. Then, the procedure returns to step S902.

Figure 10:
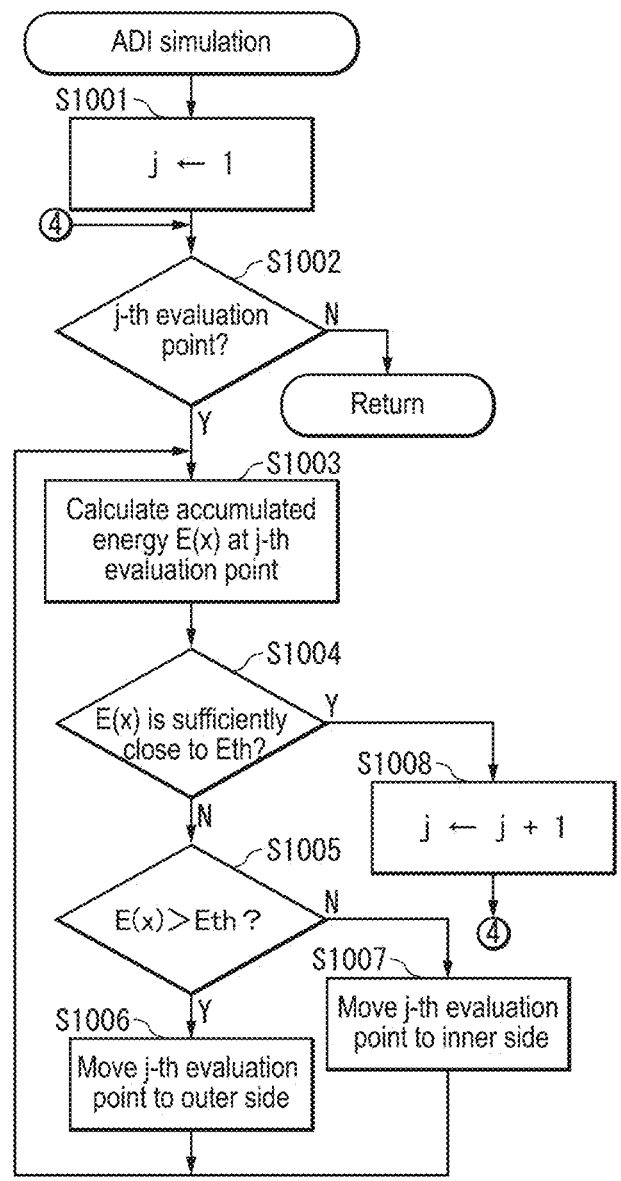
FIG. 10 is a flowchart illustrating an ADI simulation in the embodiment.

FIG. 10 is a flowchart illustrating an ADI simulation in steps S804, S805, and S904 above.

(S1001) The ADI simulation unit 131 sets an initial value 1 to a variable j. The variable j is a variable for sequentially selecting those that have not been selected, among the one or more arranged evaluation points.

(S1002) The ADI simulation unit 131 judges whether or not there is a $j^{-th}$ evaluation point. If there is a $j^{-th}$ evaluation point, the procedure advances to step S1003, and, if not, the procedure returns to the upper-level processing.

(S1003) The ADI simulation unit 131 calculates an accumulated energy E(x) at the j-th evaluation point, for example, using Numerical Formula 4.

(S1004) The ADI simulation unit 131 judges whether or not the accumulated energy E(x) is sufficiently close to the threshold Eth. The state of being sufficiently close may be, for example, a state in which the accumulated energy E(x) is close to the threshold Eth enough to be regarded as being equal to the threshold. If the accumulated energy E(x) is sufficiently close to the threshold Eth, the procedure advances to step S1005, and, if not, the procedure advances to step S1006.

(S1005) The ADI simulation unit 131 judges whether or not the accumulated energy E(x) is greater than or is greater than or equal to the threshold Eth. If the accumulated energy E(x) is greater than or is greater than or equal to the threshold Eth, the procedure advances to step S1006, and, if not, the procedure advances to step S1007.

(S1006) The ADI simulation unit 131 moves the $j^{-th}$ evaluation point to the outer side of the resist contour. Then, the procedure returns to step S1003.

(S1007) The ADI simulation unit 131 moves the $j^{-th}$ evaluation point to the inner side of the resist contour. Then, the procedure returns to step S1003.

(S1007) The ADI simulation unit 131 increments the variable j. Then, the procedure returns to step S1002.

Hereinafter, a specific operation example of the simulation apparatus 1 in this embodiment will be described.

In the factor amount converting information storage unit 111, for example four or more pieces of factor amount converting information as shown in FIG. 11 are stored. FIG. 11 is a data structure table of factor amount converting information. The factor amount converting information has, for example, a factor identifier, a shape identifier, and one or more pieces of pair information. The pair information has low-fidelity information and high-fidelity information. In the description below, a set of two or more pieces of pair information contained in the factor amount converting information may be referred to as a pair information group.

An ID (e.g., "1", "2", etc.) is associated with each of the four or more pieces of stored factor amount converting information. For example, the factor amount converting information associated with the ID "1" (hereinafter, it may be referred to as "factor amount converting information 1") has a factor identifier "opening angle $\Omega$", a shape identifier "rectangular shape (three sides)", and a pair information group "(0, 0), (0.110973, 0.09414), (0.218646, 0.183325), . . . , and (1, 1)". The pair information group is the same as the set of pairs (α, ß) consisting of two type of numerical values shown in FIG. 3.

In a similar manner, the factor amount converting information associated with the ID "2" ("factor amount converting information 2") has a factor identifier "opening angle $\Omega$", a shape identifier "recessed shape", and a pair information group including "(0.323763, 0.28542)" and the like. The factor amount converting information 3 has a factor identifier "area ratio u", a shape identifier "projecting shape", and a pair information group including "(0.27683, 0.23864)" and the like. Furthermore, factor amount converting information 4 has a factor identifier "area ratio u", a shape identifier "stepped shape", and a pair information group including "(0.113763, 0.09542)" and the like.

In the writing pattern information storage unit 112, a set of pairs each consisting of a shape identifier and a writing pattern is stored. The set of pairs each consisting of a shape identifier and a writing pattern is, for example, a pair of a shape identifier "rectangular shape (three sides)" and a writing pattern 51b, a pair of a shape identifier "recessed shape" and a writing pattern 52, a pair of a shape identifier "projecting shape" and a writing pattern 53, a pair of a shape identifier "stepped shape" and a writing pattern 54 and the like.

It is assumed that anew piece of writing pattern information indicating the writing pattern 51a shown in FIG. 5 is accepted by the accepting unit 12.

In the storage unit 11, a shape database related to various shapes of writing pattern information is stored, and the processing unit 13 recognizes the shape of the accepted writing pattern information using this shape database and acquires a shape identifier "rectangle (four sides)". The processing unit 13 accumulates the accepted writing pattern information in the writing pattern information storage unit 112 such that it is paired with the acquired shape identifier.

Next, the processing unit 13 and the like configure factor amount converting information corresponding to the accepted writing pattern information in the following procedure. That is to say, first, the ADI simulation unit 131 arranges the first number of evaluation points on a writing pattern indicated by the accepted writing pattern information. In this example, the first number is 4, and one evaluation point is arranged on each of the four sides constituting the rectangular writing pattern. The ADI simulation unit 131 performs an ADI simulation using the four evaluation points, moves each of the four evaluation points to a position at which the accumulated energy E(x) acquired using Numerical Formula 3 is close to the threshold Eth enough to be regarded as being equal to the threshold, and acquires an opening angle Q, which is a type of factor amount, and an area ratio u, which is another type of factor amount, at each of the four evaluation points after movement. Furthermore, the ADI simulation unit 131 repeats similar processing, for example, while changing one or more types of conditions among the line width and the area ratio, thereby acquiring a set of numerical values indicating the opening angle 9 and a set of numerical values indicating the area ratio u.

Next, the ADI simulation unit 131 arranges the second number of evaluation points on the writing pattern indicated by the accepted writing pattern information, the second number being larger than the first number. In this example, the second number is 24, and six evaluation points are arranged on each of the four sides constituting the rectangular writing pattern. The ADI simulation unit 131 performs an ADI simulation using the 24 evaluation points, moves each of the 24 evaluation points to a position at which the accumulated energy E(x) acquired using Numerical Formula 3 is close to the threshold Eth enough to be regarded as being equal to the threshold, and acquires an opening angle θ, which is a type of factor amount, and an area ratio u, which is another type of factor amount, at each of the four evaluation points after movement. Furthermore, the ADI simulation unit 131 repeats similar processing, for example, while changing one or more types of conditions among the line width and the area ratio, thereby acquiring a set of numerical values indicating the opening angle Q and a set of numerical values indicating the area ratio u.

Next, the processing unit 13 configures factor amount converting information corresponding to the shape identifier "rectangle (four sides)" and the factor identifier "opening angle f", using low-fidelity information, which is the set of numerical values indicating the opening angle Ω acquired in this manner using the four evaluation points, and high-fidelity information, which is the set of numerical values indicating the opening angle Ω acquired using the 24 evaluation points, and accumulates the configured factor amount converting information in the factor amount converting information storage unit 111 such that it is paired with the pair of the shape identifier "rectangle (four sides)" and the factor identifier "opening angle Ω". The processing unit 13 also configures factor amount converting information corresponding to the shape identifier "rectangle (four sides)" and the factor identifier "area ratio u", using low-fidelity information, which is the set of numerical values indicating the area ratio u acquired using the four evaluation points, and high-fidelity information, which is the set of numerical values indicating the area ratio u acquired using the 24 evaluation points, and accumulates the configured factor amount converting information in the factor amount converting information storage unit 111 such that it is paired with the pair of the shape identifier "rectangle (four sides)" and the factor identifier "area ratio u".

In this manner, a new piece of writing pattern information is added to the writing pattern information storage unit 112, and thus, in the writing pattern information storage unit 112, five pieces of writing pattern information as shown in the drawing are stored. Accordingly two types of factor amount converting information corresponding to the new piece of writing pattern information are added to the factor amount converting information storage unit 111.

Figure 12:
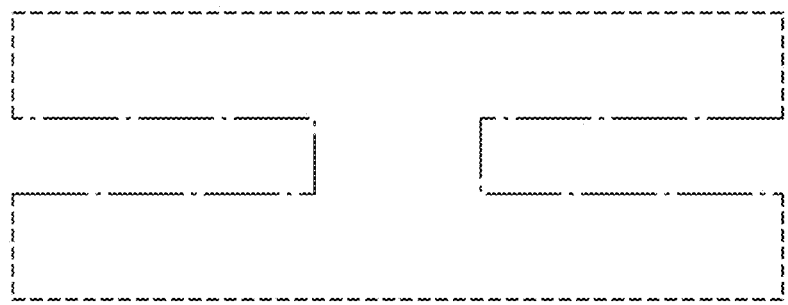
FIG. 12 is a diagram showing an example of a figure indicated by image data that is to be simulated in the embodiment.

It is assumed that, subsequently the accepting unit 12 accepts, for example, image data of a figure as shown in FIG. 12.

FIG. 12 is a diagram showing an example of a figure indicated by image data that is to be simulated. This figure is constituted by a combination of four writing patterns in total consisting of two rectangular writing patterns defined by three sides (indicated by the dotted lines) and two recessed writing patterns (indicated by the dashed dotted lines). The processing unit 13 and the like perform a simulation for the image data in the following procedure.

The processing unit 13 detects, for each of the five pieces of stored writing pattern information, a portion that matches a writing pattern indicated by the writing pattern information, in the accepted image data. In this example, two portions each corresponding to the rectangular writing pattern 51b defined by three sides and two portions each corresponding to the recessed writing pattern 52 are detected.

The ADI simulation unit 131 arranges, for each of the two portions corresponding to the rectangular writing pattern 51b defined by three sides, one evaluation point on each of the three sides constituting the portion and performs an ADI simulation, thereby acquiring a numerical value group indicating the opening angle Ω. The ADI simulation unit 131 arranges, for each of the two portions each corresponding to the recessed writing pattern 51b, one evaluation point on each of the three sides constituting the portion and performs an ADI simulation, thereby acquiring a numerical value group indicating the area ratio u as well.

Next, the converting unit 132 acquires a numerical value group of the opening angle Ω that is high-fidelity information corresponding to the low-fidelity information, which is a numerical value group of the opening angle Ω acquired by the ADI simulation unit 131, using factor amount converting information 1 corresponding to the pair of the shape identifier "rectangular shape (three sides)" and the factor identifier "opening angle Ω", among the four or more pieces of factor amount converting information 1 to 4 and the like stored in the factor amount converting information storage unit 111. For example, if the low-fidelity information acquired by the ADI simulation unit 131 is "0.110973", 0.218646", and the like, high-fidelity information "0.09414", "0.183325", and the like corresponding thereto is acquired using the factor amount converting information 1.

Furthermore, the converting unit 132 acquires a numerical value group of the opening $\Omega$u that is high-fidelity information corresponding to the low-fidelity information, which is a numerical value group of the opening angle $\Omega$ acquired by the ADI simulation unit 131, using factor amount converting information 2 corresponding to corresponding to the pair of the shape identifier "recessed shape" and the factor identifier "opening angle $\Omega$". For example, if the low-fidelity information acquired by the ADI simulation unit 131 is "0.313763" and the like, high-fidelity information "0.28542" and the like corresponding thereto is acquired using the factor amount converting information 2.

If the low-fidelity information acquired by the ADI simulation unit 131 is, for example, a numerical value group of "0.27683" and the like related to the area ratio u of the projecting writing pattern, a numerical value group "0.23864" and the like that are high-fidelity information corresponding thereto is acquired using the factor amount converting information 3.

In a similar manner, if the low-fidelity information acquired by the ADI simulation unit 131 is, for example, a numerical value group of "0.113763" and the like related to the area ratio u of the stepped writing pattern, a numerical value group "0.09542" and the like that are high-fidelity information corresponding thereto is acquired using the factor amount converting information 4.

Next, the etching simulation unit 133 performs an etching simulation using the two numerical value groups of the opening angle $\Omega$ and the two numerical value groups of the area ratio u that are high-fidelity information acquired by the converting unit 132, and acquires a function group indicating a line width change in an etch contour of the four portions.

At this time, the output unit 14 may output the information indicating a simulation result, using the function group acquired by the etching simulation unit 133. Accordingly, for example, a display screen displays a screen containing an image of a writing pattern after etching corresponding to the accepted image data, for example, as shown in FIG. 13.

Figure 13:
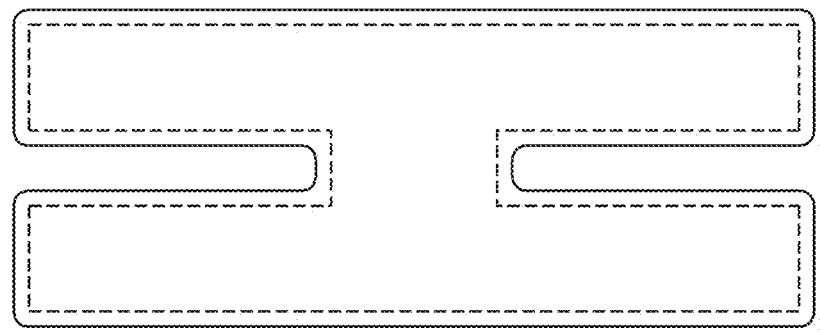
FIG. 13 is a diagram showing an output example of a simulation result in the embodiment.

FIG. 13 is a diagram showing an example of an output screen of a simulation result. On this screen, a writing pattern after etching that is a simulation result is indicated by the solid line, and an original writing pattern that has been accept and corresponds to image data is indicated by the dotted line. Instead of, or in addition to the original writing pattern, a resist contour acquired using the evaluation point group after movement by the ADI simulation unit 131 may be indicated by, for example, a dashed dotted line or the like.

Next, the judging unit 135 acquires one or more residuals using the function group indicating the line width change acquired by the etching simulation unit 133, and judges whether or not an error is small enough to satisfy a predetermined condition, using the acquired one or more residuals, and, if it is judged that the error is not small enough to satisfy the predetermined condition, the pattern information changing unit 136 changes the writing pattern information, using the function group.

At this time, the output unit 14 may output an image of the writing pattern that has been corrected, using the writing pattern information after change by the pattern information changing unit 136. Alternatively, the output unit 14 may output a moving image of the writing pattern that is being corrected, using the writing pattern information during change by the pattern information changing unit.

The processing unit 13 stores the writing pattern information after change by the pattern information changing unit 136, in the storage unit 11 or the like, in association with the writing pattern information. The writing pattern information after change stored in the storage unit 11 or the like may be transferred to an etching apparatus or the like when necessary.

As described above, according to this embodiment, a storage medium includes: a factor amount converting information storage unit 111 in which factor amount converting information, which is information indicating correspondence between low-fidelity information and high-fidelity information, is stored, wherein the low-fidelity information is one or more factor amounts with a low level of precision acquired using a first number of evaluation points, and the high-fidelity information is one or more factor amounts with a high level of precision acquired using a second number of evaluation points, the second number being larger than the first number; and a writing pattern information storage unit 112 in which writing pattern information related to a writing pattern is stored; wherein a simulation apparatus 1 performs a series of simulation processes that performs an ADI simulation using one or more evaluation points, for the writing pattern indicated by the writing pattern information, thereby acquiring one or more factor amounts, acquires high-fidelity information, which is one or more factor amounts, corresponding to the low-fidelity information, which is one or more factor amounts, using the factor amount converting information, and performs an etching simulation using the acquired one or more factor amounts. Accordingly it is possible to perform a mask process simulation accurately at high speed.

Furthermore, the simulation apparatus 1 acquires residuals respectively at the one or more evaluation points, judges whether or not an error is small enough to satisfy a predetermined condition, using the one or more residuals, and, in a case of judging that the predetermined condition is not satisfied, changes the writing pattern information using the residuals of the one or more evaluation points and repeats the series of simulation processes until it is judged that the predetermined condition is satisfied. Accordingly, it is possible to perform a mask process simulation more accurately at high speed.

Furthermore, when performing an ADI simulation, the simulation apparatus 1 arranges one or more evaluation points on an outer periphery of a writing pattern, and, until an accumulated energy for each of the one or more evaluation points becomes close to predetermined threshold enough to be regarded as being equal to the threshold, repeats processing for calculating the accumulated energy, and moving each evaluation point to the outer side of the outer periphery in a case in which the accumulated energy is greater than the threshold or moving the evaluation point to the inner side of the outer periphery in a case in which the accumulated energy is less than the threshold. When judging whether or not an error is small, the simulation apparatus 1 acquires residuals respectively at the one or more evaluation points after the accumulated energy becomes close to the predetermined threshold enough to be regarded as being equal to the threshold, and performs the judgment using the acquired one or more residuals. Accordingly, it is possible to perform a mask process simulation more accurately at high speed.

Furthermore, in the factor amount converting information storage unit 111, two or more pieces of factor amount converting information are stored in association with a shape identifier for identifying a shape of a writing pattern, the simulation apparatus 1 acquires a shape identifier for identifying a shape of a writing pattern that is specified with the writing pattern information, and acquires high-fidelity information, which is one or more factor amounts, corresponding to the low-fidelity information, which is one or more factor amounts, using factor amount converting information corresponding to the acquired shape identifier. Accordingly, it is possible to perform a proper mask process simulation according to writing patterns with multiple shapes.

Furthermore, the factor amount converting information is a pair of pieces of information consisting of the low-fidelity information that is a numerical value and the high-fidelity information that is a numerical value. Accordingly, it is possible for the simulation apparatus 1 to perform a mask process simulation accurately at high speed.

Furthermore, the factor amount converting information is a function in which the low-fidelity information is taken as input and the high-fidelity information is taken as output. Accordingly, it is possible for the simulation apparatus 1 to perform a mask process simulation accurately at high speed.

Furthermore, the function is a polynomial function or a spline function. Accordingly, it is possible for the simulation apparatus 1 to perform a mask process simulation accurately at high speed.

The processing in this embodiment may be realized by software. The software may be distributed by software downloads or the like. Furthermore, the software may be distributed in a form where the software is stored in a storage medium such as a CD-ROM. Note that the same is applied to other embodiments described in this specification. The software that realizes the information processing apparatus in this embodiment is the following sort of program.

Specifically, this program is a program using a computer-accessible storage medium including: a factor amount converting information storage unit 111 in which factor amount converting information, which is information indicating correspondence between low-fidelity information and high-fidelity information, is stored, wherein the low-fidelity information is one or more factor amounts with a low level of precision acquired using a first number of evaluation points, and the high-fidelity information is one or more factor amounts with a high level of precision acquired using a second number of evaluation points, the second number being larger than the first number; and a writing pattern information storage unit 112 in which writing pattern information related to a writing pattern is stored, the program causing a computer to function as: an ADI simulation unit 131 that performs an ADI simulation using one or more evaluation points, for the writing pattern indicated by the writing pattern information, thereby acquiring one or more factor amounts; a converting unit 132 that acquires high-fidelity information, which is one or more factor amounts, corresponding to the low-fidelity information, which is one or more factor amounts, using the factor amount converting information; and an etching simulation unit 133 that performs an etching simulation using the one or more factor amounts acquired by the converting unit 132.

Figure 14:
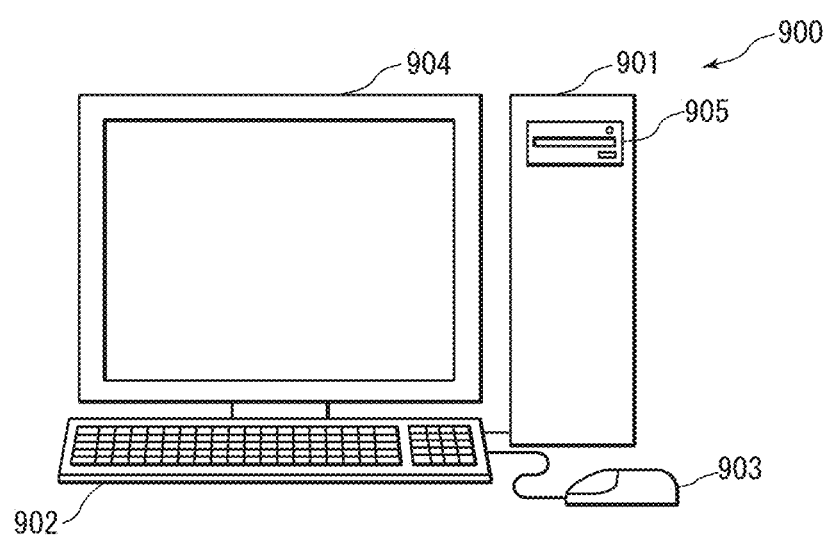
FIG. 14 is a schematic view of a computer system in the embodiment.

FIG. 14 an external view of a computer system 900 executes the programs according to the foregoing embodiments to realize the simulation apparatus 1. The foregoing embodiments may be realized using computer hardware and computer programs executed thereon. In FIG. 14, the computer system 900 includes a computer 901 including a disk drive 905, a keyboard 902, a mouse 903, and a display screen 904. The entire system including the keyboard 902, the mouse 903, and the display screen 904 may be referred to as a computer.

Figure 15:
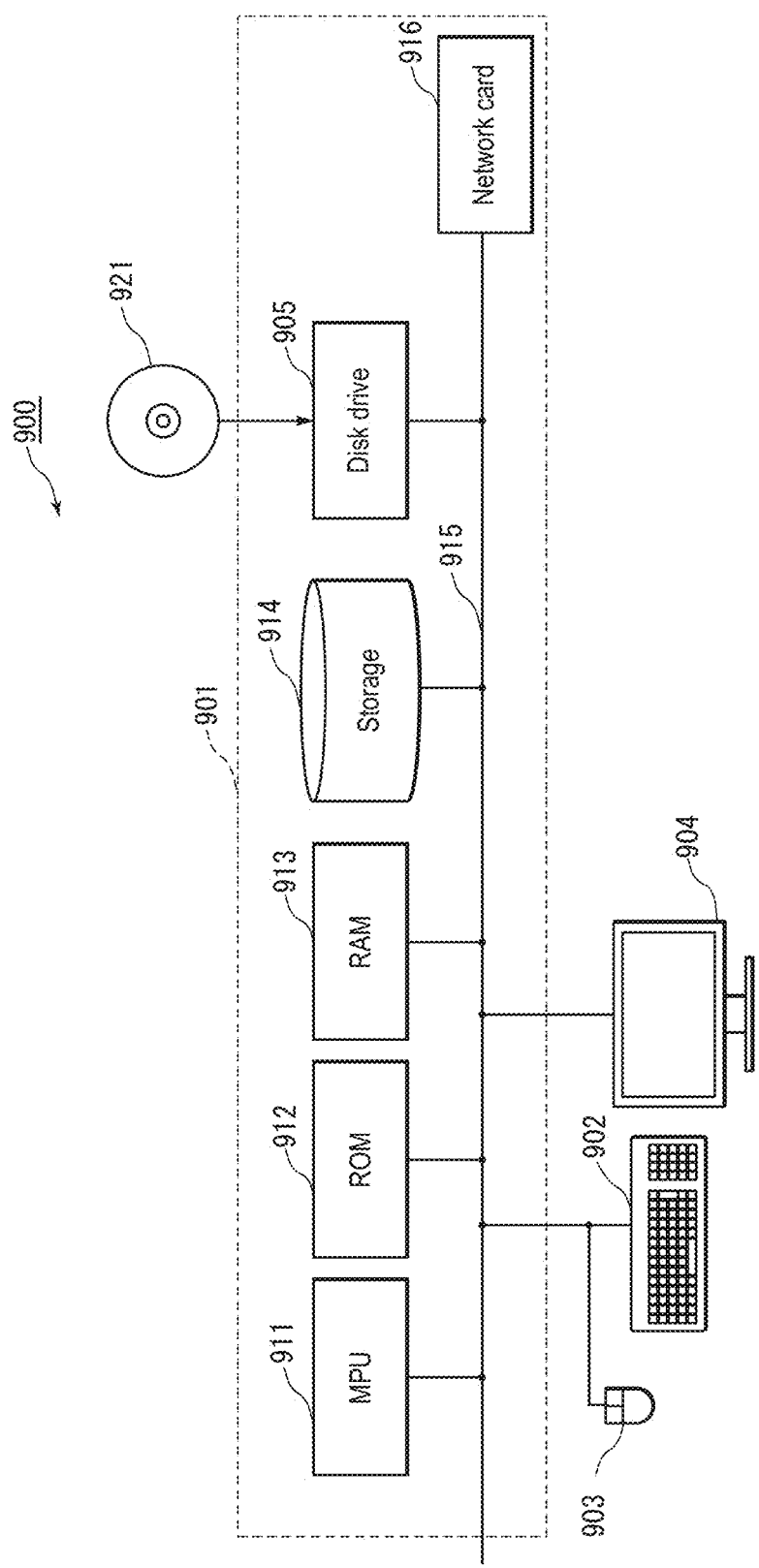
FIG. 15 is a diagram showing an example of the internal configuration of the computer system in the embodiment.

FIG. 15 is a diagram showing an internal configuration of the computer system 900. In FIG. 15, the computer 901 includes, in addition to the disk drive 905, an MPU 911, a ROM 912 in which a program such as a boot up program is to be stored, a RAM 913 that is connected to the MPU 911 and in which a command of an application program is temporarily stored and a temporary storage area is provided, a storage 914 in which an application program, a system program, and data are stored, a bus 915 that connects the MPU 911, the ROM 912, and the like, and a network card 916 for providing a connection to networks such as an internal network or an external network. Note that the storage 914 is, for example, a hard disk, an SSD, a flash memory, or the like.

The program for causing the computer system 900 to execute the functions of the simulation apparatus 1 may be stored in a disk 921 such as a DVD or a CD-ROM that is inserted into the disk drive 905 and be transferred to the storage 914. Alternatively, the program may be transmitted via a network to the computer 901 and stored in the storage 914. At the time of execution, the program is loaded into the RAM 913. The program may be loaded from the disk 921, or directly from a network. Furthermore, the program may be read by the computer system 900 via a removable storage medium other than the disk 921 (e.g., a DVD, a memory card, etc.).

The program does not necessarily have to include, for example, an operating system (OS) or a third party program to cause the computer 901 described in detail to execute the functions of the simulation apparatus 1. The program may only include a command portion to call an appropriate function or module in a controlled mode and obtain desired results. The manner in which the computer system 900 operates is well known, and thus a detailed description thereof has been omitted.

The computer system 900 described above is a server or a desktop PC, but the simulation apparatus 1 may be realized, for example, by a mobile terminal such as a laptop, a tablet device, or a smartphone. In this case, it is desirable that, for example, the keyboard 902 and the mouse 903 are replaced by a touch panel, and the disk drive 905 is replaced by a memory card slot, and the disk 921 is replaced by a memory card. Note that the description above is merely an example, and there is no limitation on the hardware configuration of the computer that realizes the simulation apparatus 1.

It should be noted that, in the programs, in a step of transmitting information, a step of receiving information, or the like, processing that is performed by hardware, for example, processing performed by a modem or an interface card in the transmitting step (processing that can be performed only by hardware) is not included.

Furthermore, the computer that executes this program may be a single computer, or may be multiple computers. That is to say, centralized processing may be performed by a single computer, or distributed processing may be performed by multiple computers.

Furthermore, in the foregoing embodiments, it will be appreciated that two or more communication parts (the receiving function of the accepting unit 12, the transmission function of the output unit 14, etc.) in one apparatus may be physically realized by one medium.

In the foregoing embodiment, each process (each function) may be realized as centralized processing using a single apparatus (system), or may be realized as distributed processing using multiple apparatuses.

It should be noted that, in the programs, in a step of transmitting information, a step of receiving information, or the like, processing that is performed by hardware, for example, processing performed by a modem or an interface card in the transmitting step (processing that can be performed only by hardware) is not included.

Furthermore, the computer that executes this program may be a single computer, or may be multiple computers. That is to say, centralized processing may be performed, or distributed processing may be performed.

Furthermore, in the foregoing embodiments, it will be appreciated that two or more communication parts (a terminal information transmitting unit, a terminal information receiving unit, etc.) in one apparatus may be physically realized by one medium.

In the foregoing embodiment, each process (each function) may be realized as centralized processing using a single apparatus (system), or may be realized as distributed processing using multiple apparatuses.

The present invention is not limited to the embodiment set forth herein. Various modifications are possible within the scope of the invention.

INDUSTRIAL APPLICABILITY

As described above, the simulation apparatus according to the present invention has an effect that it is possible to perform a mask process simulation accurately at high speed, and thus it is useful as a simulation apparatus and the like.

The invention claimed is:

1. A simulation apparatus comprising:
a factor amount converting information storage unit in which factor amount converting information, which is information indicating correspondence between low-fidelity information and high-fidelity information, is stored, wherein the low-fidelity information is one or more factor amounts with a low level of precision acquired using a first number of evaluation points, and the high-fidelity information is one or more factor amounts with a high level of precision acquired using a second number of evaluation points, the second number being larger than the first number;
a writing pattern information storage unit in which writing pattern information related to a writing pattern is stored;
an ADI simulation unit that performs an ADI simulation using one or more evaluation points, for the writing pattern indicated by the writing pattern information, thereby acquiring one or more factor amounts;
a converting unit that acquires high-fidelity information, which is one or more factor amounts, corresponding to the low-fidelity information, which is one or more factor amounts, using the factor amount converting information; and
an etching simulation unit that performs an etching simulation using the one or more factor amounts acquired by the converting unit.

2. The simulation apparatus according to claim 1, further comprising:
a judging unit that acquires residuals respectively at the one or more evaluation points using a result of the etching simulation obtained by the etching simulation unit, and judges whether or not an error is small enough to satisfy a predetermined condition, using the one or more residuals; and
a pattern information changing unit that, in a case in which the judging unit judges that the predetermined condition is not satisfied, changes the writing pattern information using the residuals of the one or more evaluation points;
wherein the processes by the ADI simulation unit, the converting unit, and the etching simulation unit are repeated until the judging unit judges that the predetermined condition is satisfied.

3. The simulation apparatus according to claim 1,
wherein, in the factor amount converting information storage unit, two or more pieces of factor amount converting information are stored in association with a shape identifier for identifying a shape of a writing pattern,
the simulation apparatus further comprises a shape identifier acquiring unit that acquires a shape identifier for identifying a shape of a writing pattern that is specified with the writing pattern information, and
the converting unit acquires high-fidelity information, which is one or more factor amounts, corresponding to the low-fidelity information, which is one or more factor amounts, using factor amount converting information corresponding to the shape identifier acquired by the shape identifier acquiring unit.

4. The simulation apparatus according to claim 1, wherein the factor amount converting information is a pair of pieces of information consisting of the low-fidelity information that is a numerical value and the high-fidelity information that is a numerical value.

5. The simulation apparatus according to claim 1, wherein the factor amount converting information is a function in which the low-fidelity information is taken as input and the high-fidelity information is taken as output.

6. The simulation apparatus according to claim 5, wherein the function is a polynomial function or a spline function.

7. A simulation method realized by: a factor amount converting information storage unit in which factor amount converting information, which is information indicating correspondence between low-fidelity information and high-fidelity information, is stored, wherein the low-fidelity information is one or more factor amounts with a low level of precision acquired using a first number of evaluation points, and the high-fidelity information is one or more factor amounts with a high level of precision acquired using a second number of evaluation points, the second number being larger than the first number; a writing pattern information storage unit in which writing pattern information related to a writing pattern is stored, an ADI simulation unit, a converting unit, and an etching simulation unit, the method comprising:
an ADI simulation step of the ADI simulation unit performing an ADI simulation using one or more evaluation points, for the writing pattern indicated by the writing pattern information, thereby acquiring one or more factor amounts;
a converting step of the converting unit acquiring high-fidelity information, which is one or more factor amounts, corresponding to the low-fidelity information, which is one or more factor amounts, using the factor amount converting information; and
an etching simulation step of the etching simulation unit performing an etching simulation using the one or more factor amounts acquired by the converting unit.

8. A non-transitory computer readable storage medium comprising:
a factor amount converting information storage in which factor amount converting information, which is information indicating correspondence between low-fidelity information and high-fidelity information, is stored, wherein the low-fidelity information is one or more factor amounts with a low level of precision acquired using a first number of evaluation points, and the high-fidelity information is one or more factor amounts with a high level of precision acquired using a second number of evaluation points, the second number being larger than the first number; and a writing pattern information storage in which writing pattern information related to a writing pattern is stored, wherein the non-transitory computer readable storage medium further comprises a program, and the program, when executed by, a computer, causes the computer to function as:

- an ADI simulation unit that performs an ADI simulation using one or more evaluation points, for the writing pattern indicated by the writing pattern information, thereby acquiring one or more factor amounts;
- a converting unit that acquires high-fidelity information, which is one or more factor amounts, corresponding to the low-fidelity information, which is one or more factor amounts, using the factor amount converting information; and
- an etching simulation unit that performs an etching simulation using the one or more factor amounts acquired by the converting unit.

* * * * *